(12) United States Patent
Hovanessian et al.

(10) Patent No.: US 8,173,767 B2
(45) Date of Patent: May 8, 2012

(54) SYNTHETIC PEPTIDE VACCINES FOR HIV: THE CBD EPITOPE AS AN EFFECTIVE IMMUNOGEN TO ELICIT BROADLY NEUTRALIZING ANTIBODIES AGAINST HIV

(75) Inventors: Ara Hovanessian, Bourg-la-Reine (FR); Jean-Paul Briand, Strasbourg (FR); Sylviane Muller, Strasbourg (FR); Bernard Krust, Paris (FR); Josette Svab, Paris (FR); Elias Said, Villejuif (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 845 days.

(21) Appl. No.: 12/073,887

(22) Filed: Mar. 11, 2008

(65) Prior Publication Data
US 2010/0247618 A1    Sep. 30, 2010

Related U.S. Application Data

(62) Division of application No. 10/820,816, filed on Apr. 9, 2004, now Pat. No. 7,364,744.

(30) Foreign Application Priority Data

Apr. 11, 2003  (EP) ..................................... 03290919

(51) Int. Cl.
*C07K 5/00* (2006.01)
(52) U.S. Cl. ........................... 530/300; 424/208.1; 435/5
(58) Field of Classification Search ........................ None
See application file for complete search history.

(56) References Cited

U.S. PATENT DOCUMENTS 6,258,782 B1 *   7/2001   Barney et al. .................. 514/1.3

OTHER PUBLICATIONS

Abaza et al. Effects of amino acid substitutions outside an antigenic site on protein binding to monoclonal antibodies of predetermined specificity obtained by peptide immunization. Journal of Protein Chemistry (1992) vol. 11, No. 5, pp. 445-454) in U.S. Appl. No. 10/820,816.*
di Marzo et al. Loss of a neutralizing epitope by a spontaneous point mutation in the V3 loop of HIV-1 isolated from an infected laboratory worker. Journal of Biological Chemistry 1993, vol. 268, No. 34, p. 25894-25901 in U.S. Appl. No. 10/820,816.*
McMichael and Hanke, HIV vaccines 1983-2003. Nature Medicine 2003, vol. 9, p. 875-880 in U.S. Appl. No. 10/820,816.*
Pazner (Identifying epitopes of HIV-1 that induce protective antibodies, Nature Immunology 2004, vol. 4, p. 199-210in U.S. Appl. No. 10/820,816.*

* cited by examiner

*Primary Examiner* — Agnieszka Boesen
(74) *Attorney, Agent, or Firm* — Finnegan, Henderson, Farabow, Garrett & Dunner, LLP

(57) ABSTRACT

The present invention relates to peptides, referred to as CBD-1, CBD-2, CBM-1/TH-1, CBM-1/TH-2, CBM-2/TH-1, CBM-2/TH-2 and C-20 peptides, which are antigenic and elicit a protective immune response against HIV infection. Compositions, pharmaceutical compositions and vaccines comprising these antigenic peptides are also encompassed by the present invention, as well as neutralizing antibodies which inhibit infection of primary CD4+ T lymphocytes by various HIV isolates. Methods for diagnosis of HIV are also disclosed.

10 Claims, 19 Drawing Sheets

Figure 1:
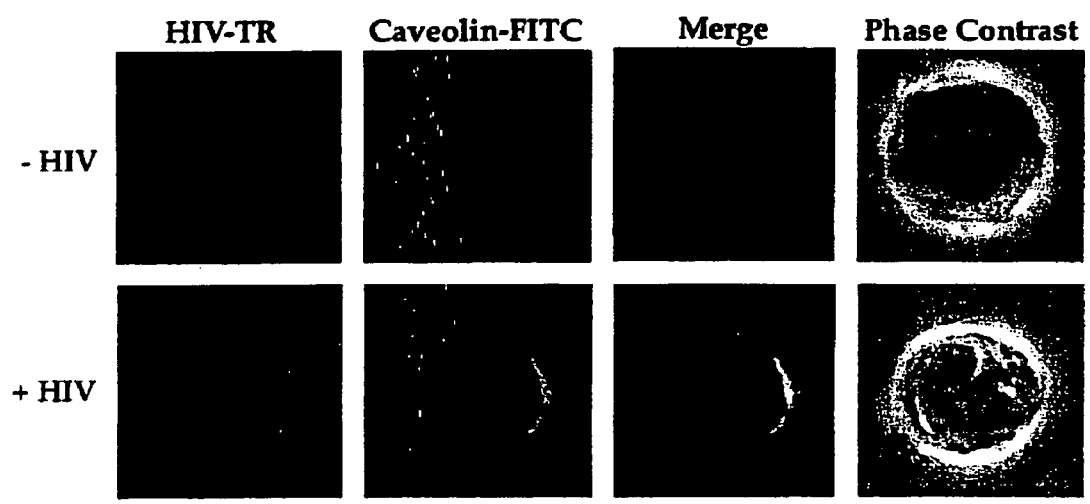

Consensus Sequence in the gp41 Ectodomain Containing the Caveolin Binding Motif (-W-X-X-X-X-W-X-X-W-)

W = Conserved (D,N)　(D)　　　　(90-97%)

619　　　　　　　　　　　　　　　　　　　633
L - E - E - I - W - N - N - M - T - W - M - E - W - E - R (Q)　(D,S)　(>97%)　　　　　　　　(K)

FIGURE 4

Consensus sequence in the HIV TM glycoprotein ectodomain containing the
Caveolin Binding Motif (-W-X-X-X-X-W-X-X-W-)

| | 619 | | | | | | | | | | | | | | 633 |
|---|---|---|---|---|---|---|---|---|---|---|---|---|---|---|---|
| HIV-1 Consensus | L | - | E | - | I | - | W | - N - N - M - T - | W | - | M | - | E | - | W - E - R |
| HIV-1 LAI | L | - | E | - Q - I - | W | - N - N - M - T - | W | - | M | - | E | - | W - D - R |
| HIV-1 Ba-L | L | - | N | - K - I - | W | - D - N - M - T - | W | - | I | - | E | - | W - D - R |
| HIV-1 ELI | L | - | N | - E - I - | W | - Q - N - M - T - | W | - | H | - | E | - | W - E - R |
| HIV-1 92UG037 | Q | - | D | - E - I - | W | - N - N - M - T - | W | - | L | - | Q | - | W - D - K |
| HIV-1 92BR025 | Q | - | E | - D - I - | W | - N - N - M - T - | W | - | M | - | Q | - | W - D - R |
| HIV-2 ROD | L | - | A | - P - D - | W | - D - N - M - T - | W | - | Q | - | E | - | W - E - K |
| HIV-2 EHO | L | - | K | - P - D - | W | - N - N - M - T - | W | - | Q | - | Q | - | W - E - R |
| SIVagm | L | - | T | - P - D - | W | - N - N - D - T - | W | - | Q | - | E | - | W - E - R |
| SIVsm | L | - | T | - P - D - | W | - D - N - M - T - | W | - | Q | - | E | - | W - E - R |
| CBD1 | L | - | E | - Q - I - | W | - N - N - M - T - | W | - | M | - | Q | - | W - D - K |

FIGURE 5

CBD1-FITC 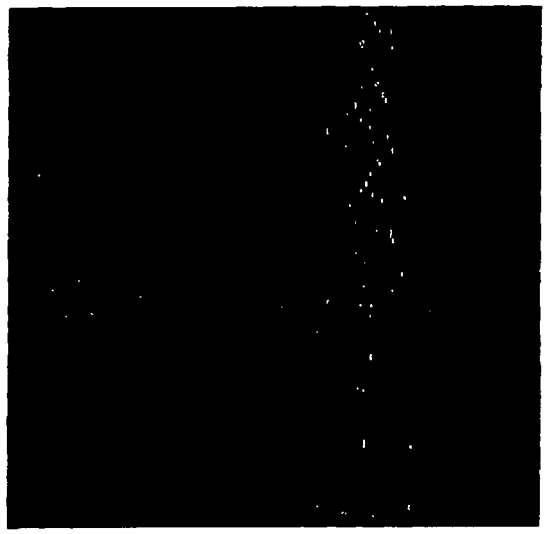 Phase Contrast 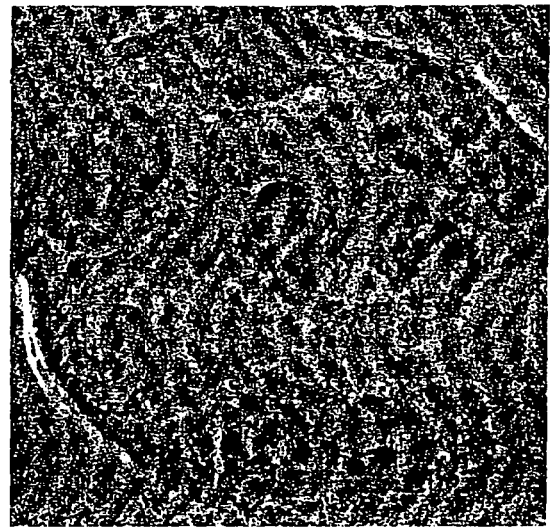
FIGURE 7

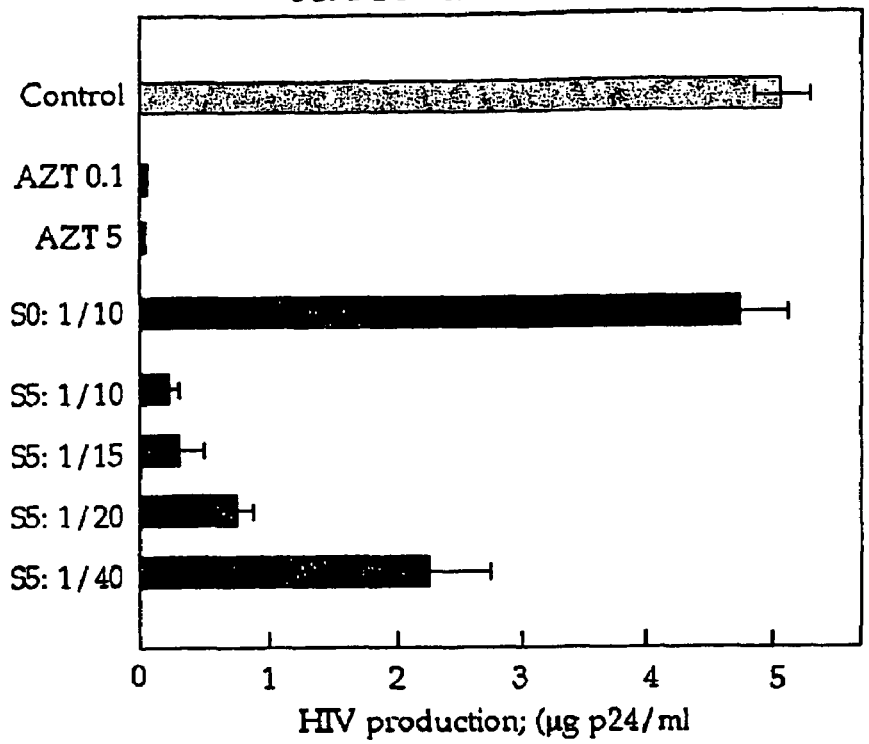
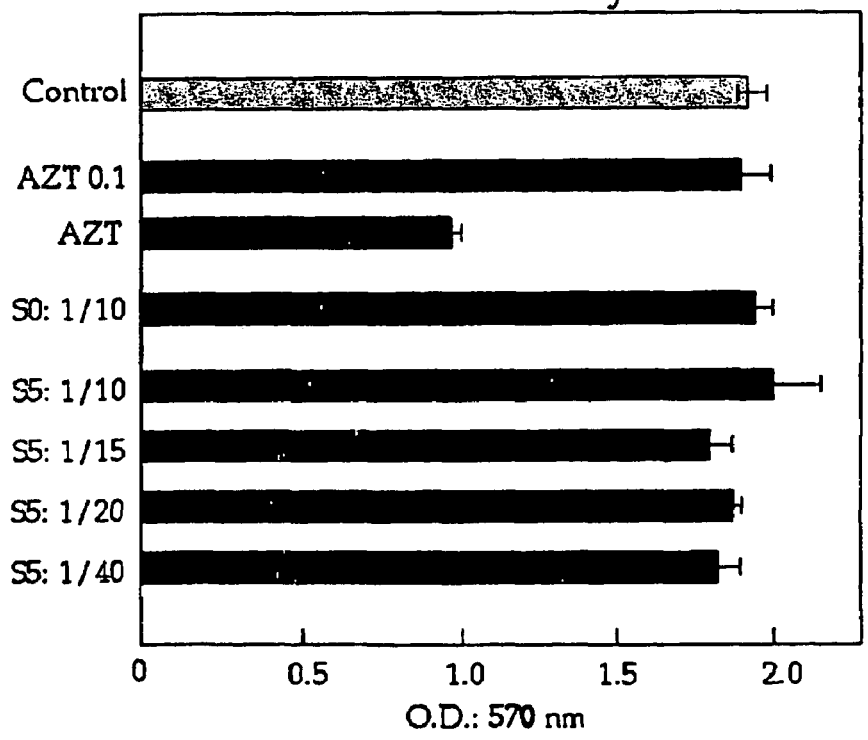
FIGURE 10

Effect of anti-CBD1 on HIV infection
Serum added with HIV and at 90' & 3 days p.i.
A.
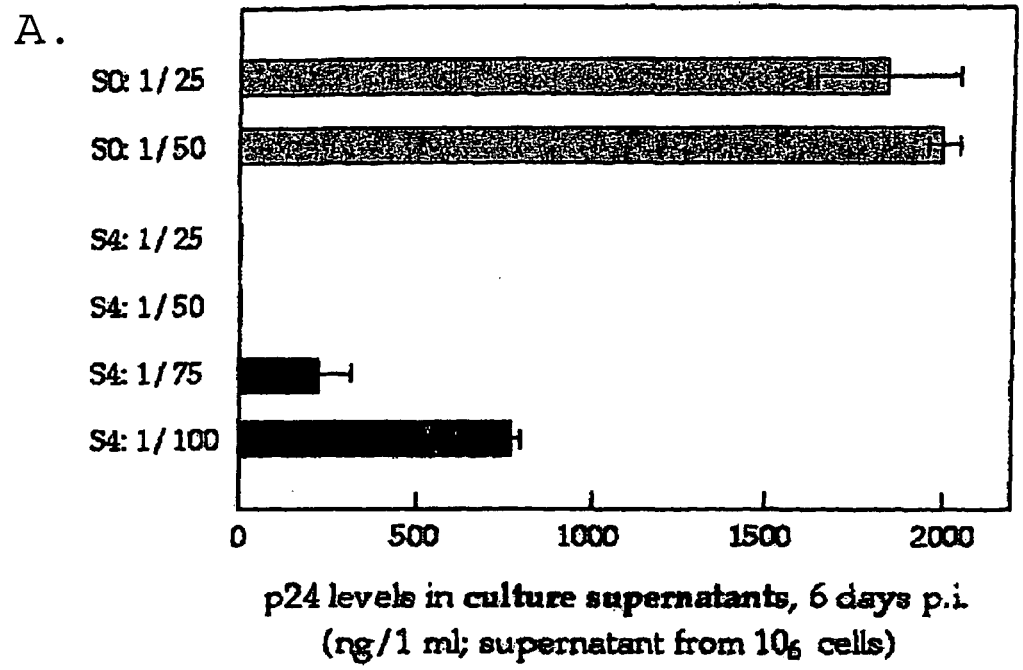
p24 levels in culture supernatants, 6 days p.i.
(ng/1 ml; supernatant from 10⁶ cells)
B.
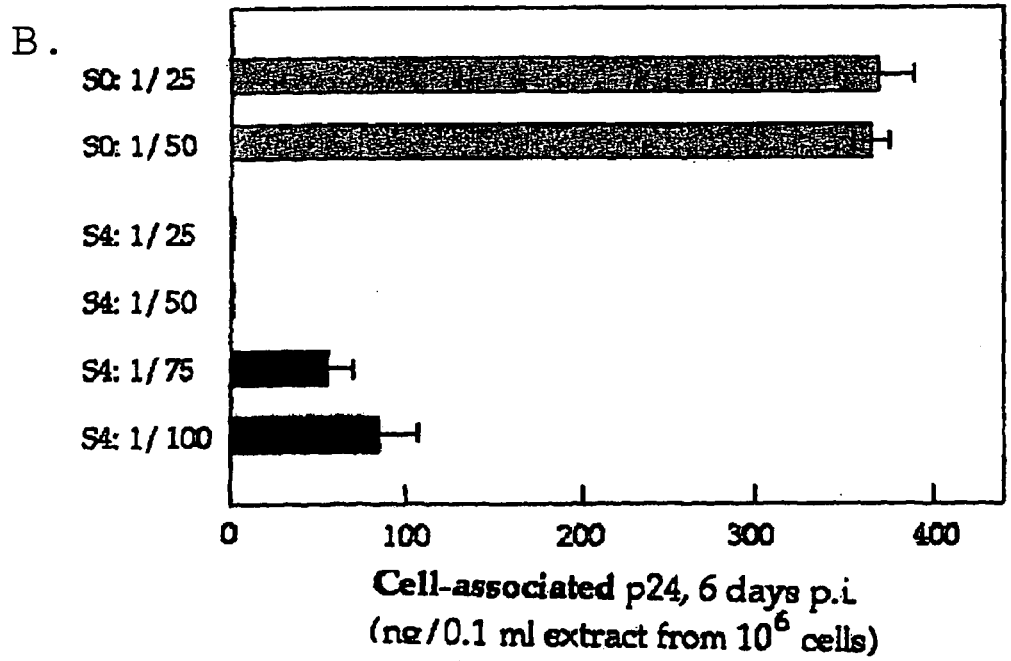
Cell-associated p24, 6 days p.i.
(ng/0.1 ml extract from 10⁶ cells)
FIGURE 13

SYNTHETIC PEPTIDE VACCINES FOR HIV: THE CBD EPITOPE AS AN EFFECTIVE IMMUNOGEN TO ELICIT BROADLY NEUTRALIZING ANTIBODIES AGAINST HIV

This is a division of application Ser. No. 10/820,816, filed Apr. 9, 2004, now issued as U.S. Pat. No. 7,364,744, which claims priority from European Patent Application (EPO) No. 03290919.4, filed Apr. 11, 2003, all of which are incorporated herein by reference.

BACKGROUND AND PRIOR ART

The present invention relates to peptides, referred to as CBD-1, CBD-2, CBM-1/TH-1, CBM-1/TH-2, CBM-2/TH-1, CBM-2/TH-2 and C-20 peptides, which are immunogenic and elicit a protective immune response against HIV infection in vitro. Pharmaceutical or therapeutical compositions and vaccines comprising these antigenic peptides are also encompassed by the present invention, as well as neutralizing antibodies which inhibit HIV infection and, when added to already infected cells, cause the production of defective HIV particles. Methods for diagnosis of HIV are also disclosed.

The gp41 molecule of HIV-1 is a transmembrane protein with several important features within its ectodomain (amino acids residues 512 to 681; the numbering is according to Dong et al. (1). First, the amino terminus of gp41, created by proteolytic cleavage of the gp160 precursor, contains a hydrophobic, glycine-rich "fusion" peptide that is essential for membrane fusion. Second, there are two α-helix containing domains at the N- and C-terminal of gp41 with a sequence motif characteristic of coiled coils. Between these two α-helix domains there is the immunodominant domain including a small loop. The two α-helix containing domains are arranged in very stable six-helix bundles. Three N-helices (amino acids 545-590) form an interior, parallel coiled-coil trimer, while three C-helices (amino acids 628-661) pack in an oblique, antiparallel manner into highly conserved, hydrophobic grooves on the surface of this trimer. This structure likely represents the core of fusion-active gp41 (2, 3). A synthetic peptide referred to as T-20 (amino acids 638-673 of gp41), corresponding to the C-helix domain of gp41, was shown to block HIV-induced fusion entry in cell cultures and HIV-infection in virus-infected individuals (4, 5). The mechanism of this inhibition is due to the binding of the T-20 peptide to the N-helix domain. Thus, by blocking the entry of HIV into normal cells is one means to arrive at inhibiting HIV-infection.

Lipid rafts are known to play an important role during the HIV entry process into target cells (6). Lipid rafts are glycolipid-enriched membrane microdomains, which are fundamental in the lateral organization of the plasma membrane by forming platforms that are implicated in the clustering of membrane proteins, endocytosis, signal transduction and membrane trafficking (7, 8, 9, 10). Lipid rafts contain sphingolipid and cholesterol-based structures that are associated with specific membrane proteins such as glycosylphosphatidylinositol (GPI)-linked proteins CD59 and CD90 Lipid rafts containing caveolin as the defining protein component are known as caveolae. Caveolins bind cholesterol directly, which stabilizes the formation of caveolin homo-oligomeric complexes (10). While lipid rafts appear to be small in size and dispersed all around the plasma membrane of non-polarized cells, the interaction of raft-associated proteins with their ligands or their cross-linking with antibodies lead to the oligomerization of raft components (9, 11).

Lipid rafts with their associated proteins can be isolated by virtue of their insolubility in the non-ionic detergent, Triton X-100® (8). A number of pathogens including viruses have been reported to use lipid rafts and caveolae as the endocytosis route or by exerting their pathogenic effects (7, 12). In the case of HIV-1, several groups have reported the implication of lipid rafts in the viral entry (6, 13, 14) and budding processes (15,16,17).

HIV-1 infects target cells by the capacity of its envelope glycoproteins gp120-gp41 complex to attach cells and induce the fusion of virus to cell membranes, a process which leads to virus entry (18). The external envelope glycoprotein contains the binding site for the CD4 receptor and an hypervariable region of about 36 amino acids referred to as the V3 loop. The transmembrane glycoprotein contains a potential fusion peptide at its amino terminus, which is implicated in the membrane fusion process. The external and transmembrane glycoproteins (gp120-gp41 for HIV-1) are associated in a noncovalent manner to generate a functional complex. gp120 determines viral tropism by binding to target-cell receptors, while gp41 mediates fusion between viral and cellular membranes. The receptor complex essential for HIV entry into cells consists of the CD4 molecule and at least one member of the chemokine receptor family; CCR5 is the major coreceptor for macrophage-tropic HIV-1 isolates (R5), whereas for T-lymphocyte-tropic isolates (X4) the major coreceptor is CXCR4 (19, 20). Several observations have also pointed out that the initial attachment of HIV particles to target cells occurs through the co-ordinated interaction of the V3 loop with the cell-surface-expressed heparan sulfate proteoglycans and nucleolin (21, 22, 23, 24).

Consistent with the implication of lipid rafts in the HIV-1 entry process, CD4, CXCR4 and CCR5 partition and signal in rafts after gp120-induced clustering (14) or cross-linking of the cell-surface-bound HIV particles (6), while the functioning of CD4 and chemokine receptors appears to require their association in lipid rafts (25, 26). Depletion of cellular cholesterol by the drug, β-cyclodextrin, renders primary cells and cell lines highly resistant to HIV-1 mediated syncytium formation and also to infection by both X4 and R5 HIV-1 strains (27). Epithelial transcytosis of HIV-1 also uses the lipid raft pathway as a transport mechanism to get from the apical side to the basolateral side of the cell (28). In addition, lipid rafts have been shown to play a critical role in HIV-1 assembly and release that takes place at the plasma membrane. Both HIV-1 Gag and envelope protein appear to be associated with lipid rafts, a process which is necessary for the assembly of HIV proteins at the plasma membrane and for the budding of virions (16, 17). Recently, the coexpression of caveolin-1 with HIV-1 has been reported to block virus production mostly by inhibiting viral protein synthesis, although some minor effects on HIV budding were not excluded (15). The region in caveolin-1 responsible for this latter inhibitory effect was found to be the hydrophobic, membrane-associated domain (residues 101 to 135), whereas the first 100 N-terminal amino acids, which include the oligomerization and scaffolding domains, were shown to be dispensable (15). Finally, transcytosis of HIV across epithelial cells have been shown to be mediated by the capacity of virus particles to bind glycosphingolipid galactosyl ceramide receptors in caveolae (28).

Caveolae are a specialized form of lipid rafts defined by the presence of a specific protein marker, caveolin. They have a unique lipid composition, mainly composed of cholesterol and sphingolipids (10). There are multiple forms of caveolin: caveolin-1 and caveolin-2 are expressed as stable heterooligomeric complexes within most cell types, while caveolin-3 is restricted to striated muscle cells. Recent observations have pointed out that cells implicated in HIV infection, such as lymphocytes, macrophages, and dendritic cells express caveolin-1 at the cell surface (Harris et al., 2002). Caveolin-1 contains 178 amino acid residues. Its central hydrophobic domain (amino acids 102-134) is thought to form a hairpin-like structure within the membrane with both the N-terminal domain (amino acids 1-101) and the C-terminal domain (amino acids 135-178) facing the cytoplasm. A short domain at amino acids 82 to 101 in caveolin has been defined as caveolin-scaffolding domain which is responsible for the formation of multivalent homo-oligomers of caveolin and also represents a domain implicated in the interaction of caveolin with different ligands (for reviews see (10, 41)). By using caveolin-scaffolding domain as a receptor, Lisanti and collaborators have selected caveolin-binding peptide motifs from phage display libraries (40, 41). Two related caveolin-binding motifs have been defined: φXφXXXXφ and φXXXX-φXXφ, where φ is an aromatic amino acid Trp, Phe, or Tyr, whereas X is any other amino acid.

In view of the implication of lipid rafts in HIV entry and budding process (12), any substance that interferes with the functioning of lipid rafts during HIV infection, would inhibit HIV entry and/or budding process and thus be an effective tool to treat and/or prevent HIV-infection.

Ever since the discovery and isolation of LAV by Barre-Sinousi, Chermann and Montagnier in 1983 at the Pasteur Institute a search for effective treatment without major side effects and prevention of AIDS has been elusive.

Treating patients with AIDS with a combination of reverse transcriptase and drugs that target HIV's protease enzyme, known in the art as "highly active antiretroviral therapy," is effective to drive the viral load in blood to low levels.

Thus, since 1996, antiretroviral drugs such as zidovudine (AZT), ritonavir, saquinavir, lamivudine, amprenavir, abacavir, idinavir, nelfinavir and the like, were generally used in triple-drug therapy using two reverse transcriptase inhibitors and one protease inhibitor, to reduce the amount of HIV in patients. However, none of these drugs entirely eliminates the virus.

Moreover, there remains serious problems associate with the triple-drug therapy. Not only must an HIV-infected person take the drugs on a consistent schedule and for the duration of life, but these drugs are not only quite expensive ($10,000 annually or more), but toxic. Due to their toxic nature, antiretroviral drugs have known side effects which include nausea, vomiting, diarrhea, anemia, lipodystrophy, diabetes-like problems, brittle bones, numbness, tingling or pain in the hands or feet, and heart disease. As a result of these side effects many AIDS patients stop taking their medication.

Besides their toxic effects, one of the major difficulties with highly active retroviral therapy is drug resistance. Since HIV is known to constantly mutate, billions of new HIV viruses are produced in the body every day. These mutations change parts of the virus often rendering the drugs ineffective.

A better solution to treat HIV is to entirely eliminate the virus by the use of immunogens that can induce humoral and cellular immune responses against HIV (42). In view of this, epitopes in the surface gp120 and transmembrane gp41 envelope glycoproteins of HIV-1 have been investigated in great detail.

The principal targets of neutralizing antibodies against HIV-1 are the surface and transmembrane envelope glycoproteins gp120 and gp41 (43). The HIV-1 gp120 contains three major targets for the action of neutralizing antibodies, the CD4 binding domain, the third hypervariable domain referred to as the V3 loop, and a conserved region between the V1/V2 and V3 loop that appears to be responsible for the binding of R5/X4 virus to their respective chemokine receptor. Several neutralizing monoclonal antibodies have been raised against gp120, whereas against gp41 only neutralizing human monoclonal antibodies have been isolated from HIV-infected individuals. One such human monoclonal antibody is MAb CL3 that recognizes 10 amino acids within the immunodominant region in gp41 (44). Another type of neutralizing human monoclonal antibodies are directed against the membrane-proximal external region of gp41 (amino acids 657-671) containing the ELDKWA epitope of MAb 2F5, known as the "Katinger epitope" (45). However, it should be noted that synthetic peptides corresponding to these specific epitopes in gp41 fail to elicit the production of neutralizing antibodies albeit generating peptide specific high titered antibodies (46, 47). Similarly, antisera raised against synthetic peptides corresponding to the N- and C-terminal heptad repeats in gp41 are nonneutralizing although they are capable of reacting with gp41 (for references see Golding et al., 2002; 48). Thus, epitope vaccines have so far been unsuccessful because they have failed to elicit neutralizing antibody production. Consistent with the capacity of neutralizing antibodies to control HIV infection, several studies have demonstrated that neutralizing antibodies directed against HIV-1 envelope glycoprotein could prevent infection in primates and accelerate clearance of cell-free virions from the blood (49, 50).

Thus, vaccines are currently being developed such as cellular vaccines, which stimulate T-cell immunity, antibody vaccines, peptide vaccines, naked DNA vaccines, multi-valent virus vaccines such as recombinant carnarypox vaccines and combination vaccines such as a DNA vaccine combined with a fowlpox vaccine. However, due to HIV's extraordinary mutability and evolution into multiple subtypes or clades worldwide, an HIV vaccine prepared from one HIV clade may not be effective against a different clade or even within a given clade.

To overcome the problems associated with different existing clades, novel vaccines have been developed and clinical trials are underway with a vaccine that incorporates HIV genetic material from clades A, B and C. However, this does not solve the problem of AIDS patients that have the remaining HIV clades D, E, F, G, H, I, J and O. It should be emphasized that autologous neutralizing antibodies can be isolated from patients eight to ten weeks after HIV infection. However after a period of one-year, the early virus population loses its sensitivity to neutralization as it becomes replaced by mutated strains that are resistant to neutralization (51). Thus an efficient immunogen for the generation of neutralizing antibody production should represent a conserved domain in HIV envelope glycoproteins, and which does not undergo selective pressure because of the essential function in the HIV infectious cycle.

The synthetic peptide inhibitor T20 (29) blocks cell fusion and HIV-1 entry into non-infected host cells by disrupting the conformational changes in gp41 during the HIV-induced fusion process. T-20, known as Fuzeon™, is currently being experimentally tested in HIV-infected individuals. However tolerance to long term administration of T-20 and its toxicity remain at this time, unknown. Moreover, there is a rapid emergence of resistant HIV-1 in patients receiving T-20 (52). Another disadvantage of T-20 is that the treatment protocol uses very high amount (100 mg) of this synthetic peptide administered daily in order to obtain a potent inhibition of HIV infection.

Due to the HIV-1 worldwide epidemic, the search for drug treatments and vaccines for HIV-1 has taken a prime stage over other medical diseases, including HIV-2. Treatments and vaccines for HIV-2 have not been fervently pursued as much as HIV-1 since HIV-2 infection occurs more slowly and there is lower viral load in HIV-2 infected persons.

Thus, there is a need in the art for vaccines and pharmaceutical compositions to treat and/or prevent all forms of immunodeficiency viruses such as HIV-1, HIV-2 and SIV for all clades.

There is also a need in this art to provide vaccines or pharmaceutical compositions to treat and/or prevent all forms of immunodeficiency viruses for all clades at lower costs, with fewer side effects and which have less drug resistance.

In one aspect, the present invention provides peptides and variants of such peptides capable of eliciting neutralizing antibodies that block HIV infection. In another aspect of the invention these peptides are antigens.

In another aspect, the present invention provides antigens and variants of such antigens that are capable of eliciting broadly neutralizing antibodies that block infection by various types and subtypes of HIV.

In still another aspect the present invention concerns the peptides or the antigens according to the invention associated covalently or non-covalently with peptides corresponding to the V3 loop and/or any HIV-1 or HIV-2 envelope protein or glycoprotein or/and a foreign antigen of interest such as HBs (surface antigen of the hepatitis B virus) as described in U.S. Pat. No. 5,314,808 or LSA3 antigen from *Plasmodium falciparum* as described in U.S. Pat. No. 6,191,270. In this regard, the present invention also includes mixtures of the peptides or antigens with other antigens known In the art.

In yet another aspect the present invention provides a vaccine for prevention of HIV-infection.

In still another aspect, the present invention provides a pharmaceutical composition as a therapeutic vaccine for treating HIV.

In yet another aspect, the present invention provides antibodies raised against the antigens and antigen variants. These antibodies are used in immunotherapy to prevent and/or treat HIV-infection. Neutralizing antibodies that are used in passive vaccines are also disclosed.

In still another aspect, the present invention provides natural neutralizing antibodies against the antigen and antigen variants. These natural antibodies are used in immunotherapy to prevent and/or treat HIV infection. Methods for the preparation of human monoclonal antibodies are also disclosed.

In yet another aspect, the present invention provides a method or use of the antibodies to detect HIV. Kits are also disclosed.

In still another aspect, the present invention provides a method to detect specific antibodies in HIV infected individuals. Kits are also disclosed.

In yet another aspect, the present invention provides a method of treating and/or preventing AIDS. Use of the antigens and antibodies to treat HIV is also disclosed.

In yet another aspect, the present invention provides a purified peptide comprising at least one of the sequences of SEQ ID Nos. 1 to 18 and their use to isolate anti-HIV molecules.

In yet another aspect, the present invention provides a complex of caveolin bound to the peptides of SEQ ID Nos. 1 to 9 and 11 to 18 to prevent HIV infection.

These and other aspects are achieved by the present invention as evidenced by the summary of the invention, description of the preferred embodiments and the claims.

SUMMARY OF THE INVENTION

The present invention thus relates to a pharmaceutical composition comprising at least one peptide comprising at least one of the following peptide sequences:

WXXXXWXXW        (SEQ ID No. 1)

where W is a tryptophan or an aromatic amino acid and X is any amino acid that is not aromatic or a pharmaceutically acceptable salt of said at least one peptide or a variant of SEQ ID No. 1 provided that said variant immunologically reacts with antibodies raised against a CBD-1 peptide or a CBD-2 peptide; and a pharmaceutically acceptable vehicle.

The present invention also provides a pharmaceutical composition wherein the peptide contained in the composition is selected from at least one of the following amino acid sequences:

(SEQ ID NO. 2)
L-E-Q-I-W-N-N-M-T-W-M-Q-W-D-K: a CBD-1 peptide sequence;

(SEQ ID NO. 3)
L-T-P-D-W-N-N-M-T-W-Q-E-W-E-R: a CBD-2 peptide sequence;

(SEQ ID No. 4)
C-T-T-A-V-P-W-N-A-S-W-S-N-K-S-L-E-Q-I-W-N-N-M-T-W-M-Q-W-D-K: a CBM-1/TH-1 peptide sequence;

(SEQ ID No. 5)
C-H-T-T-V-P-W-P-N-D-S-L-T-P-D-W-N-N-M-T-W-M-Q-W-D-K: a CBM-1/TH-2 peptide sequence;

(SEQ ID No. 6)
C-H-T-T-V-P-W-P-N-D-S-L-T-P-D-W-N-N-M-T-W-Q-E-W-E-R: a CBM-2/TH-2 peptide sequence;

(SEQ ID No. 7)
C-T-T-A-V-P-W-N-A-S-W-S-N-K-S-L-E-Q-I-W-N-N-M-T-W-Q-E-W-E-R: a CBM-2/TH-1 peptide sequence;

(SEQ ID No. 8)
W-N-N-M-T-W-M-E-W; and (SEQ ID No. 9)
W-N-N-M-T-W-Q-E-W or variants of the peptide sequences which comprise amino acid additions, deletions and/or substitutions in SEQ ID No. 2 or SEQ ID No. 3 or SEQ ID No. 4 or SEQ ID No. 5 or SEQ ID No. 6 or SEQ ID No. 7 or SEQ ID No. 8 or SEQ ID No. 9 provided that said variants immunologically reacts with antibodies raised against SEQ ID Nos. 2 to 9.

In yet another aspect, the present invention provides a composition comprising at least one of the peptides of SEQ ID Nos. 2 to 9.

In yet another aspect, the present invention provides a pharmaceutical composition or a composition, wherein said at least one peptide has 90% to 99.9999% sequence homology to SEQ ID Nos. 1 to 9.

In another aspect, the present invention provides a pharmaceutical composition or a composition, wherein said at least one peptide is glycosylated, has introduced therein two cysteine residues to form a disulfide bridge or is phosphorylated.

In still another aspect of the invention, the above-mentioned pharmaceutical composition or composition comprises at least one peptide which has linker sequences attached to the N- or C-terminals. In this regard, the linker sequences are fatty acids.

The at least one peptide comprised in the pharmaceutical compositions or compositions of the invention is an antigen.

The invention also concerns the use of the composition or the pharmaceutical composition according to the invention for producing a drug and these compositions may used to make a vaccine.

Therefore, a vaccine comprising at least one of the peptides as described herein or a pharmaceutically acceptable salt thereof and a pharmaceutically acceptable vehicle is embraced by the present invention.

In addition to the above mentioned components, vaccines, compositions and pharmaceutical compositions may further comprise an adjuvant.

In another aspect of the invention, the vaccine, the compositions and the pharmaceutical compositions can be presented in a multimeric or polyvalent manner.

In another aspect of the invention, the vaccine, the compositions or the pharmaceutical compositions can be encapsulated with a polymer, liposome or micelle.

The present invention also relates to nucleic acids encoding SEQ ID Nos. 1 to 9 such as the CBD-1, CBD-2, CBM-1/TH-1, CBM-1-TH-2, CBM-2/TH-2 and CBM-2/TH-1 peptide sequences or variants of these peptide sequences such as, for example, SEQ ID Nos. 11 to 18.

The present invention also relates to antigens that comprise any one of the sequences of SEQ ID Nos. 1 to 9 and variants thereof. These antigens elicit protective immunity against HIV.

In yet another aspect, the present invention also relates to an immunogenic antigen that elicits the generation of a protective immunity against HIV. This antigen comprises the following amino acid sequence:

```
                                    (SEQ ID No. 10)
D-G-I-W-K-A-S-F-T-T-F-T-V-T-K-Y-W-F-Y-R
a C-20 peptide sequence.
```

Use of the peptides or the antibodies described herein to treat or prevent HIV infection is encompassed by the present invention.

Monoclonal antibodies, polyclonal antibodies, oligoclonal antibodies or antibodies with a restricted specificity, as well as neutralizing antibodies raised against the peptides or peptide variants containing the HIV-specific caveolin-binding motif (CBM) as described herein are also encompassed by the present invention.

In another aspect a method for detecting the presence of HIV in a biological sample, comprising contacting the biological sample taken from a mammal with an antibody specifically directed against HIV under conditions that allow the formation of an immunological complex; and detecting the immunological complex that is formed is also part of the present invention.

In yet another aspect, the present invention also relates to a method for screening a biological sample for the existence of natural neutralizing antibodies and selection of cells producing such neutralizing antibodies from HIV-infected individuals.

Kits containing the peptides or antibodies are another aspect of the present invention.

The present invention provides a purified peptide comprising at least one of the sequences of SEQ ID Nos. 1 to 18 or variants thereof having 90% to 99.9999% homology to SEQ ID Nos. 1 to 18. Their use to isolate anti-HIV molecules is also embraced by the invention.

The present invention also relates to a method of selecting or isolating anti-HIV molecules comprising attaching the above purified peptides to a solid support; incubating with a caveolin preparation or with the C-20 peptide in the presence of anti-HIV molecules that prevent the interaction of caveolin or the C-20 peptide with said attached antigens; and selecting or isolating said anti-HIV molecules.

The present invention also provides the use of a complex of caveolin or the C-20 peptide bound to the peptides of SEQ ID Nos. 1 to 9 and 11 to 18 to prevent HIV infection.

BRIEF DESCRIPTION OF THE DRAWINGS

FIG. 1 are photographs from a laser scanning confocal immunofluorescence microscopy experiment illustrating HIV induced aggregation of caveolin-1 in the plasma membrane of MT4 cells.

FIG. 2 is a dot-immunoblot analysis showing the recovery of caveolin in detergent insoluble higher density fractions containing also HIV-1 p24, p17 and gp41.

FIG. 3 is a schematic view of the transmembrane envelope glycoprotein gp41 showing important functional regions.

FIG. 4 is a schematic representation showing the amino acid consensus sequence of the HIV-specific Caveolin-Binding Domain 1 (CBD-1) in gp41 containing the conserved caveolin-binding motif, WXXXXWXXW.

FIG. 5 shows the alignment of the consensus amino acid sequence in gp41 showing the HIV-specific caveolin-binding motif WXXXXWXXW, which is conserved in the transmembrane envelope glycoprotein among HIV-1, HIV-2 and SIV isolates.

FIG. 6 is an autoradiography showing the binding of biotinylated CBD-1 peptide to caveolin in crude cell extracts.

FIG. 7 are photographs from a laser scanning confocal immunofluorescence microscopy experiment showing the entry of the CBD-1 peptide into cells.

FIG. 8 are graphs of the results from an ELISA of serum collected from the immunized rabbit named "Aldernay" using two different types of ELISA plates coated with the CBD-1 peptide. FIG. 8 A shows the ELISA results obtained using a PVC plate, while in FIG. 8B Maxisorp plates were used. The optical density (OD) was measured at 450 nm. An OD value above 0.20 was considered positive. These graphs illustrate the titration of the different sera collected from the immunized rabbit with the CBD-1 peptide.

FIG. 9 is a graph showing HIV production of p24 from 2 to 8 days post-infection in the presence of rabbit sera from "Aldernay" preimmune S0 and immune S5. This graph illustrates the effect of anti-CBD-1 antibodies on the HIV infectious cycle. The insert entitled HIV pellet is a section of Western immunoblotting showing the bands of the HIV core and matrix protein, p24 and p17, respectively, that are found in the HIV particles recovered from the culture supernatant. This section illustrates that HIV particles are not detectable in cultures treated with the immune S0 serum.

FIG. 10A is a histogram of p24 levels of culture supernatants from cells treated with pre-immune S0 and immune S5 serum from "Aldernay" at specific dilutions 6 days post infection (p.i.). This histogram illustrates that addition of anti-CBD-1 antibodies at 2 days post-infection inhibits HIV infection in a dose dependent manner. The mean of ±S.D. (standard deviation) of duplicate samples is shown.

FIG. 10B is a histogram showing results of MT4 cells infected with HIV-1 LAI and treated with S0 and S5 serum from "Aldernay" at 6 days post-infection. The cell cultures were assayed for cell viability using the MTT (3-(4,5-dimethylthiazol-2-yl)-2,5-diphenyltetrazolium bromide) test. Each histogram represents the mean±S.D. (standard deviation) of quadruplicate samples. The results show that the immune serum has no apparent effect on cell viability.

FIG. 11 is an immunoblot of MT4 cells infected with HIV-1 LAI and at 2 days post-infection, the cells were suspended in fresh culture medium supplemented with a 1/10 dilution of the pre-immune serum from "Aldernay" (lanes P) or the immune serum from "Aldernay" (lanes I). In a parallel experiment cells were infected without any treatment (lane C) or treated with 1 μM of AZT. Cells (panel Cells) and HIV extracts (panel HIV) were analyzed using human positive HIV serum (section A) or the anti-p17 antibody (section B). The position of the precursor Gag p55 and its cleaved products p40, p24 and p17 are shown on the right. This figure illustrates that the addition of anti-CBD-1 antibodies at 2 days post-infection inhibits HIV infection and the overall HIV particle production.

FIGS. 12A and B are histograms of the results from an ELISA assay of p24 concentration levels, 6 days post-infection of MT4 cells incubated with HIV-1 LAI and supplemented with rabbit sera from "Aldernay" before immunization S0 and after each immunization (S1 to S6) at a 1/20 dilution. FIG. 12A is an ELISA of p24 levels in culture supernatants, while FIG. 12B is an ELISA of p24 levels in cells extracts. The mean of ±S.D. (standard deviation) of duplicate samples is shown.

FIG. 13 comprises histograms of the p24 ELISA levels of the anti-CBD-1 serum S0 and S4 from the rabbit "Aldernay" at various dilutions in HIV-1 LAI infected MT4 cells at 6 days post-infection. FIG. 13 A is the analysis of the culture supernatants, while FIG. 13 B is the analysis of the cell extracts. These histograms show a dose-dependent inhibition of HIV infection reaching >99% inhibition at a 1/50 dilution of S4. The degree of inhibition of S4 at a 1/75 and a 1/100 dilution was 88% and 60%, respectively.

Figure 14:
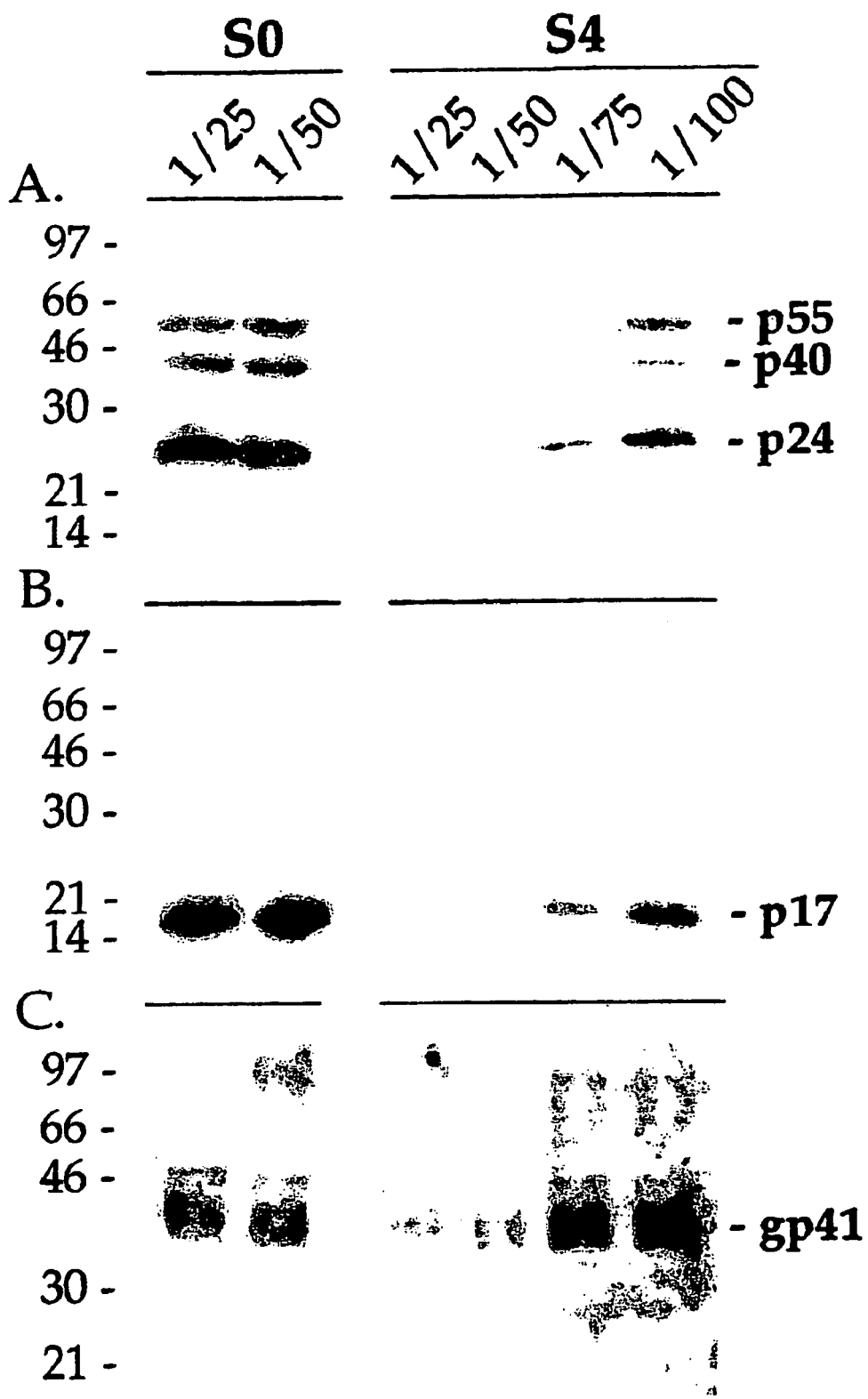

FIG. 14 is an immunoblot of extracts from HIV-infected MT4 cells at 6 days post-infection. Triton X-100 soluble extracts were analyzed by immunoblotting for the presence of Gag proteins (sections A and B; 12.5% gel for PAGE), whereas Triton-insoluble pellets were analyzed by immunoblotting for gp41 after solubilization in PAGE sample buffer containing 1% SDS (section C; 10% gel for PAGE). Infected cells has been treated with the pre-immune serum S0 (at 1/25 and 1/50 dilution) and the immune serum S4 (at 1/25, 1/50, 1/75 and 1/100 dilution) as in FIG. 13. The results show the enhanced accumulation of gp41 in the Triton resistant pellet obtained from HIV-infected cells cultured in the presence of increasing dilutions of the S4 serum. The enhanced accumulation of gp41 in the Triton resistant pellet in HIV-infected cells, point out that that HIV particles produced in cultures treated with anti-CBD-1 antibodies should produce defective virus particles which should manifest lower infectivity. Consequently, anti-CBD-1 antibodies have two distinct mode of actions: a marked effect on early stages and a significant effect on later stages of the HIV infectious cycle.

Figure 15:
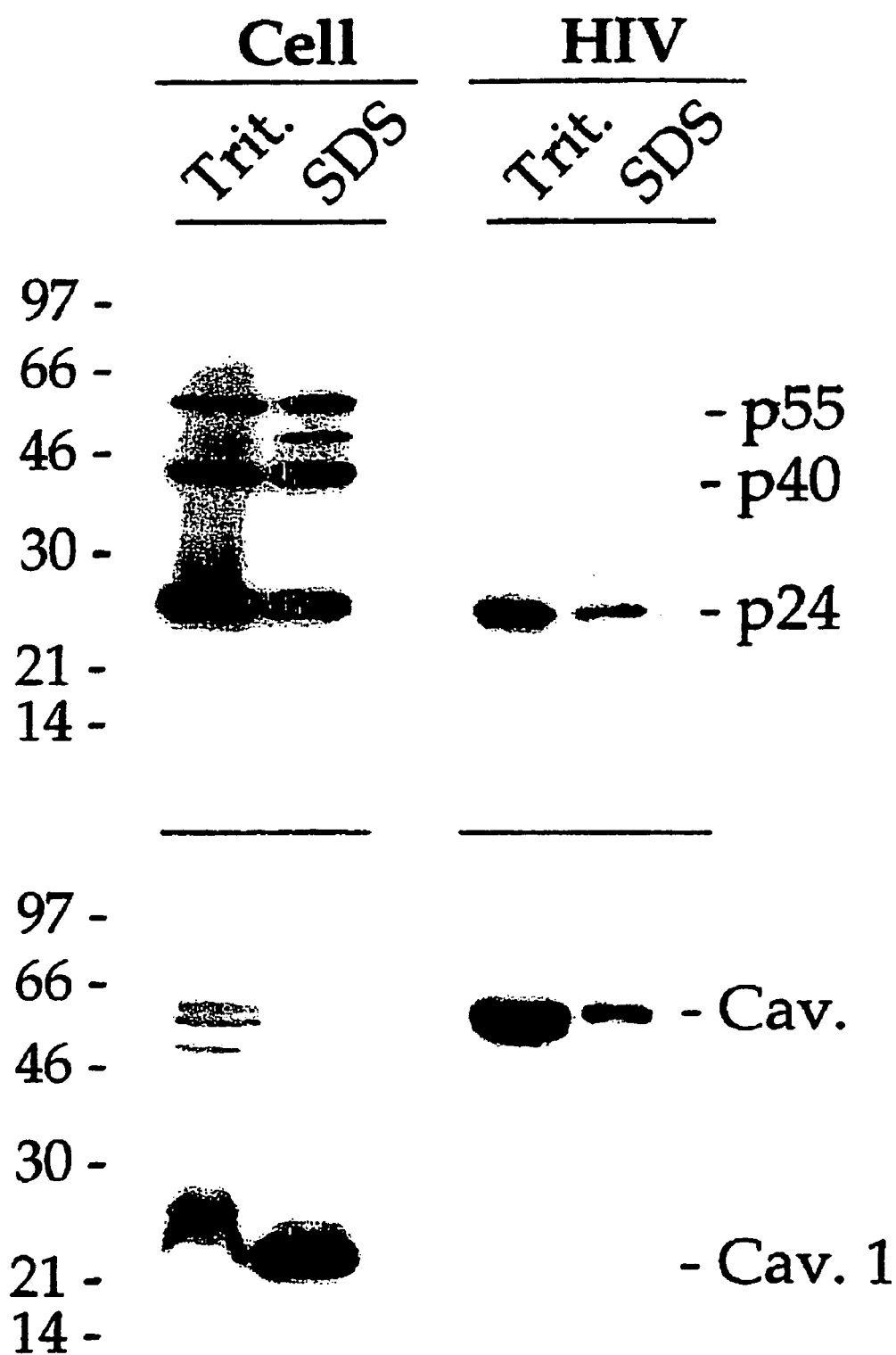

FIG. 15 is an immunoblot showing the incorporation of caveolin-1 in HIV particles. At 7 days post-infection with HIV-1 LAI, M4T cells were extracted in the 1% Triton X-100 containing lysis buffer (10 mM Hepes pH 7.6, 150 mM NaCl, 2.5 mM $MgCl_2$, 1% Triton) and the Triton-insoluble pellet was solubilized in the PAGE sample buffer containing 1% SDS. The culture supernatant of the infected cells was centrifuged at 100,00 g and the HIV pellet was extracted in the Triton lysis buffer whereas the triton-resistant pellet was suspended in the PAGE buffer. Triton and SDS soluble fractions from the infected cells and from the HIV pellet were analyzed by immunoblotting using rabbit anti-caveolin 1 antibodies, rabbit anti-p24 antibody, and monoclonal antibody against actin, gp120, and gp41. In cell extracts caveolin is mainly soluble in SDS whereas in HIV particles caveolin is mainly soluble in Triton. Note the modification in PAGE migration profile of caveolin associated with the HIV pellet.

Figure 16:
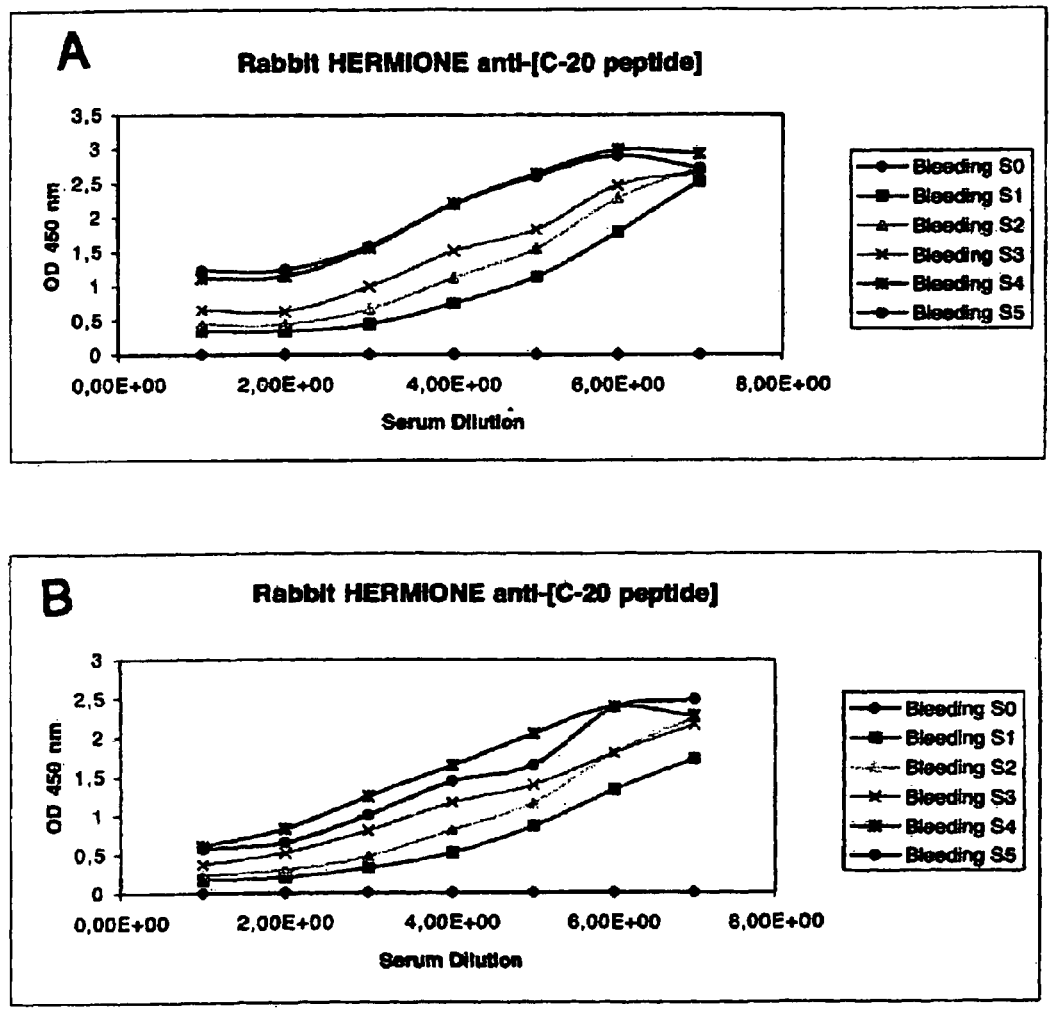

FIG. 16 are graphs of the results from an ELISA of serum collected from the immunized rabbit named "Hermione" using two different types of ELISA plates coated with the C-20 peptide. FIG. 16A shows the ELISA results obtained using a PVC plate, while in FIG. 16B Maxisorp plates were used. The optical density (OD) was measured at 450 nm. An OD value above 0.20 was considered positive.

Figure 17:
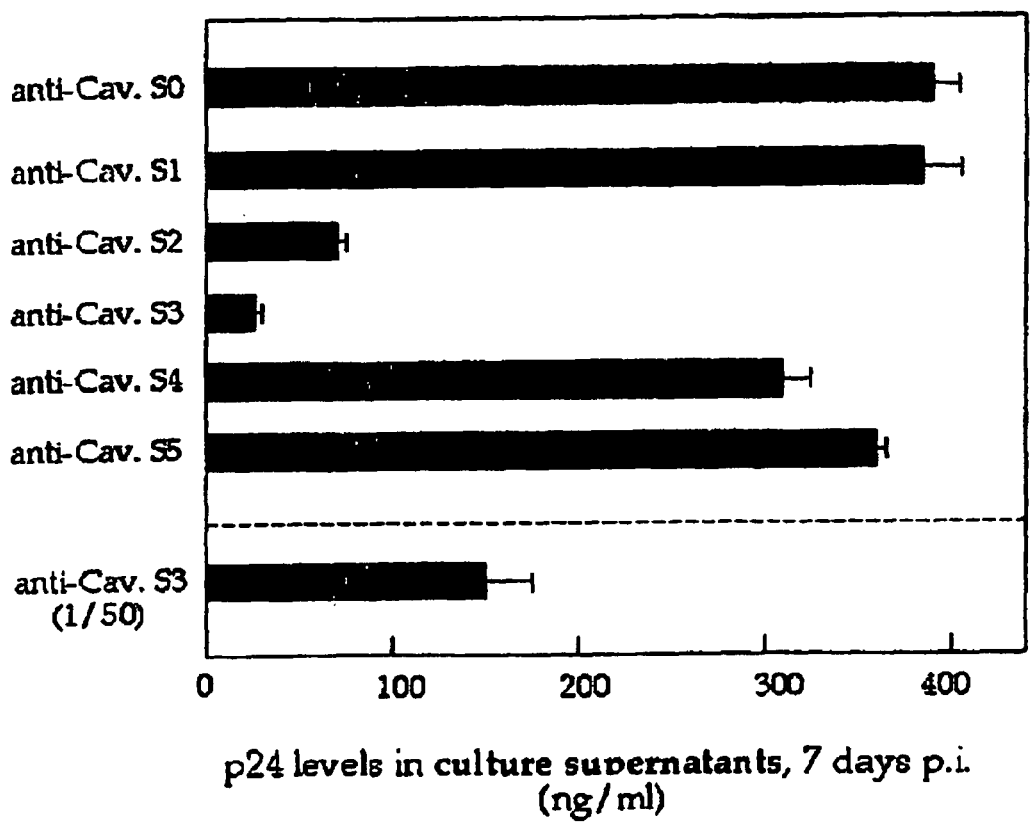

FIG. 17 is a histogram of the results of p24 ELISA levels of culture supernatants of anti-caveolin serum from the rabbit "Hermione" at a 1/25 dilution in HIV-1 LAI infected MT4 cells at 7 days post-infection. The results show that immune serum raised against the C-20 peptide (S2 and S3) inhibits HIV infection.

Figure 18:
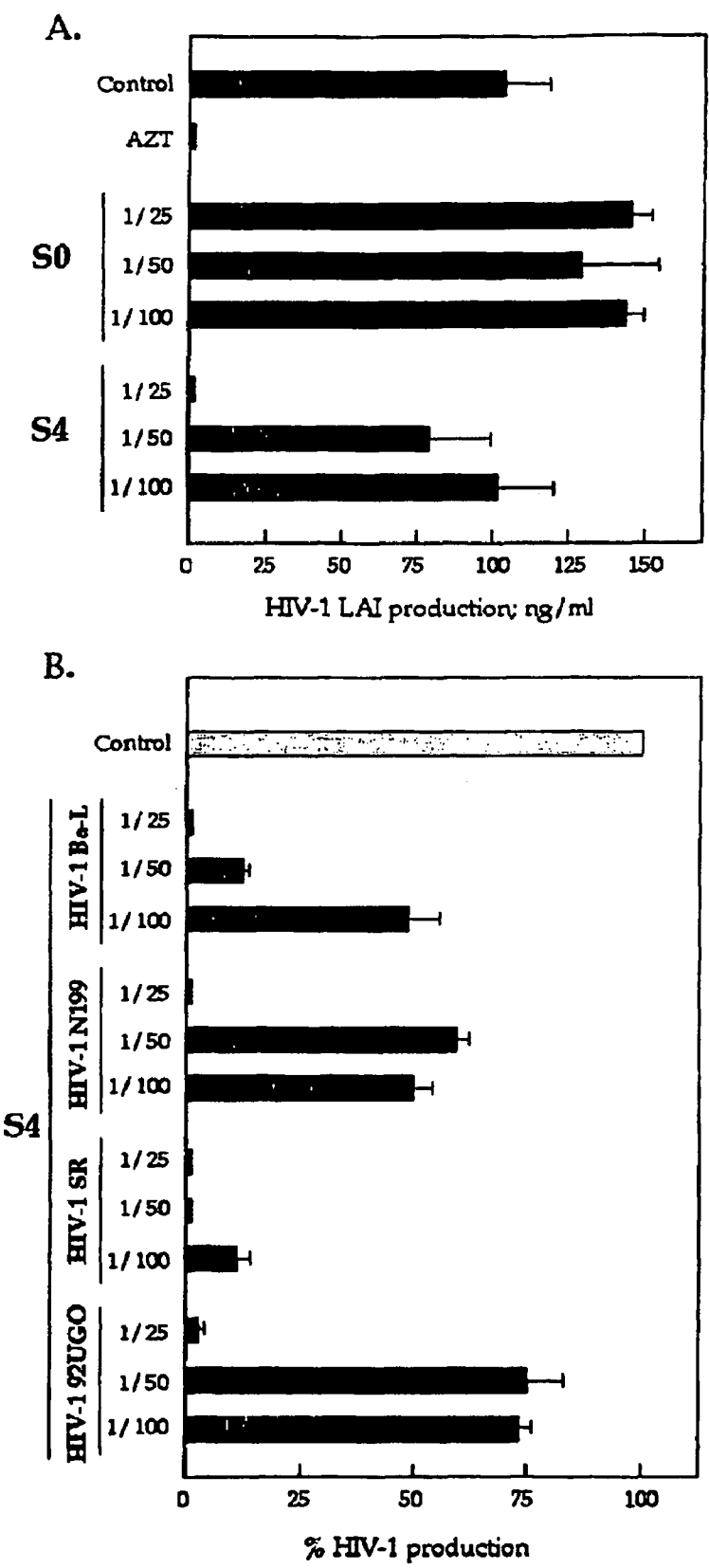

FIG. 18 are histograms of % HIV production in culture supernatants at 5 days post-infection of primary $CD4^+$ T lymphocytes by T-lymphocyte tropic (X4) HIV-1 LAI, macrophage-tropic (R5) HIV-Ba-L, an isolate resistant to the nonnucleoside RT inhibitor nevirapine (HIV-1, N199), an isolate resistant the HIV protease inhibitor saquinavir (HIV-1 SR), and the primary isolate HIV-1 92UGO37 from Uganda. Infections were carried out in the absence (histogram control), or in the presence of the pre-immune serum S0 (at 1/25, 1/50, and 1/100 dilution) and the immune serum S4 (at 1/25, 1/50, and 1/100 dilution) as it is indicated. HIV production was monitored by p24 ELISA in the culture supernatants. In section A, the production of HIV-1 LAI is presented in infected lymphocytes in the absence (Control) and presence of AZT (0.1 µM). For each virus isolate, the % production of HIV was calculated in respect to the production observed in the presence of the preimmune serum S0. The mean of ±SD of duplicate samples is shown. The results show a significant inhibition of HIV virus infection in primary cultures by the anti-CBD-1 antibodies.

Figure 19:
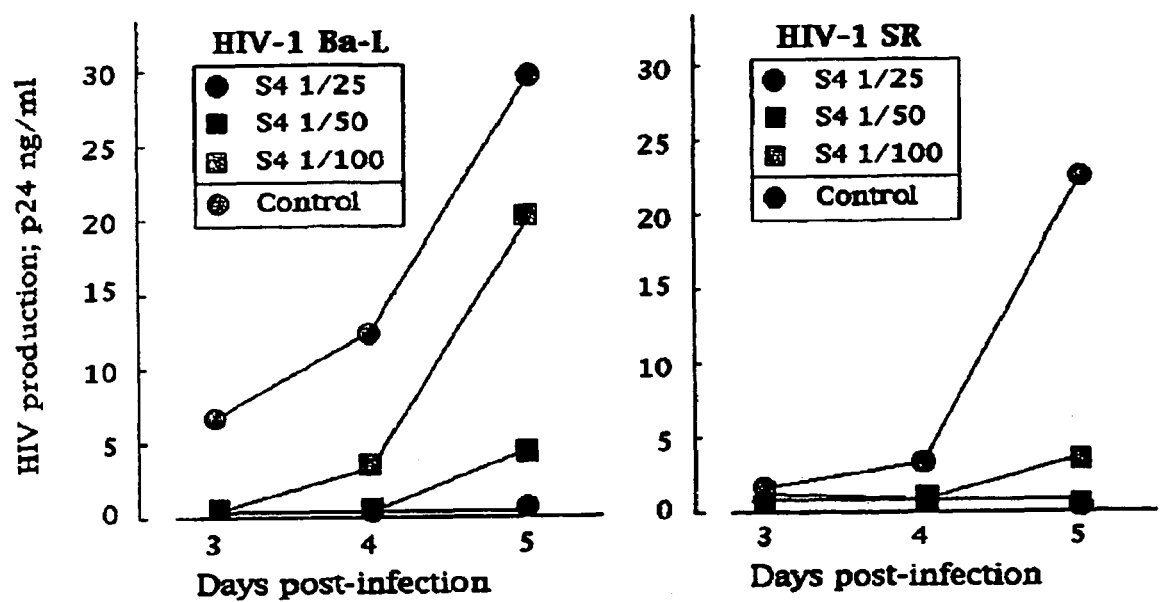

FIG. 19 are graphs showing the kinetics of inhibition of HIV infection by the anti-CBD-1 antibodies against R5 HIV-1 Ba-L and the isolate resistant to the HIV protease inhibitor saquinavir HIV-1 SR in primary $CD4^+$ T lymphocyte culture in the absence (Control) or presence of the immune serum S4 at 1/25, 1/50, and 1/100 dilutions (as it is indicated in the figure). Culture supernatants at 3, 4, and 5 days post-infection were assayed by ELISA for the concentration p24. Each point represents the mean of duplicate samples.

PREFERRED EMBODIMENTS OF THE INVENTION

As used herein, the term "HIV" encompasses any immunodeficiency syndrome that is prevalent in mammals such as HIV-1, HIV-2 and SIV, as well as all clades of HIV-1, HIV-2 and SIV.

The term "clades" means subtypes of HIV, which are genetically distinct, but are all infectious. Glades that are well known in the art include clades A, B, C, D, E, F, G, H, I, J and O. It will be appreciated that different clades that are not well defined within the art at the filing of the present invention are also included in the overall definition of clades and are encompassed by the present invention.

The word "peptide" refers to carbon chain comprising several amino acids glycosylated or non-glycosylated and carrying any post-transductional modification on at least one amino acid.

The word "antigen" refers to a molecule (for example a peptide) that provokes an immune response such as, for example, a T lymphocyte response or a B lymphocyte response or which can be recognized by the immune system. In this regard, an antigen includes any agent that when introduced into an immunocompetent animal stimulates the production of a cellular-mediated response or the production of a specific antibody or antibodies that can combine with the antigen.

As used herein, the term "foreign antigen" refers to any antigen except antigens from HIV or SIV.

The term "antibody" used generically herein, encompasses polyclonal antibodies, monoclonal antibodies, oligoclonal antibodies and antibodies with a restricted specificity.

The term "epitope" refers to that portion of an antigenic molecule (for example, a peptide) that is specifically bound by an antibody combining site.

The term "bound" when referring to the complex of caveolin bound to the peptide of the present invention and more specifically SEQ ID Nos. 1 to 9 and 11 to 15 means held together in a complex.

The term "nucleic acid" means a molecule encoding genetic information, composed of nucleotide subunits. This term refers to DNA (deoxyribonucleic acid) as well as RNA (ribonucleic acid). DNA can be genomic DNA extracted from biological material or complementary DNA (cDNA) synthesized from a messenger RNA template. RNA can be total RNA, ribosomal RNA, messenger RNA (mRNA) or double stranded RNA (dsRNA) as described in WO0244321 and WO0168836.

The term "neutralizing antibody" means an antibody that influences the HIV particle in such a way that the replicative cycle of the virus becomes inhibited at an early phase of virus infection or virus release is blocked, or causes the production of defective virus particles which are not infectious.

As used herein, the term "CBM" means a caveolin-binding motif. CBM-1 refers to those sequences in HIV-1, while CBM-2 refers to those sequences in HIV-2.

As used herein the term "CBD-1 peptide" refers to a caveolin-binding domain peptide corresponding to amino acids 619 to 633 in HIV-1, the numbering being according to the consensus amino acid sequence of the gp41 ectodomain (1, 39, 53), which peptide is immunogenic. "CBD-1 peptide" also encompasses variants of this peptide, which include amino acid substitutions, deletions and additions.

As used herein the term "CBD-2 peptide" refers to a caveolin-binding domain peptide corresponding to amino acids 662 to 676 in HIV-2, the numbering being according to the consensus amino acid sequence of the transmembrane envelope glycoprotein ectodomain (1, 39, 53), which peptide is immunogenic. "CBD-2 peptide" also encompasses variants of this peptide, which include amino acid substitutions, deletions and additions.

As used herein, the terms "CBM-1/TH-1 peptide, CBM-1/TH-2 peptide, CBM-2/TH-2 peptide, CBM-2/TH-1 peptide" refer to antigens corresponding to the region in the ectodomain of the transmembrane envelope glycoprotein of HIV, amino acid residues 604 to 633 in HIV-1 and amino acid residues 651 to 676 in HIV-2 (1), that contains the caveolin-binding motif (CBM). CBM-1/TH-1 peptide, CBM-2/TH-2 peptide, CBM-2/TH-2 peptide, CBM-2/TH-1 peptide" also encompasses variants of this peptide, which include amino acid substitutions, deletions and additions.

As used herein the term "C-20 peptide" refers to a peptide found in the scaffolding domain of caveolin from amino acids 82 to 101 of caveolin 1, which peptide is immunogenic. "C-20 peptide" "also encompasses variants of this peptide which include amino acid substitutions, deletions and additions.

Variants also include peptides that have a specific sequence identity with the CBD-1, CBD-2, CBM-1/TH-1, CBM-1/TH-2, CBM-2/TH-2, CBM-2/TH-1 or the C-20 peptide. "Sequence identity" means, for example, that in a sequence having 60% sequence identify, 60% identical amino acids are present in the same position upon alignment of the sequences, which alignment can be performed by known methods in the art.

"Antigen variants" or "variants" when referred to in the present invention are capable of or can immunologically react with CBD-1, CBD-2, CBM-1/TH-1, CBM-1/TH-2, CBM-2/TH-2, CBM-2/TH-1 or C-20 antibodies.

The term "specifically reacts with" means that the antigen or antigen variant is specifically recognized by antibodies raised against the antigen or antigen variant. The term "specifically" when referring to antibody recognition of an antigen means that no cross-reaction occurs.

"Immunological reacts with" when referring to the antigen variants of the present invention means that these antigens bind to the antibodies of the CBD-1, CBD-2, CBM-1/TH-1, CBM-1/TH-2, CBM-2/TH-2, CBM-2/TH-1 or C-20 antigens.

The term "passive vaccine" means a vaccine conferring temporary protection against an infection upon administration to an individual.

As used herein the term "pharmaceutical composition" encompasses a medicinal substance having an active ingredient in a mixture or formulation that can be used to treat or prevent HIV in human beings as well as in animals.

The term "vaccine" refers to any preparation having an active ingredient of an immunogenic material suitable for the stimulation of active immunity in mammals without inducing the disease.

Unless stated otherwise all peptide sequences set forth herein are presented from the $NH_2$-terminal end towards to the COOH-terminal end and all nucleic acid sequences set forth herein are presented from the 5' end to the 3' end.

The present invention relates in a very general manner to a composition comprising conserved epitopes. One of these conserved epitopes is present in the CBD-1 and the CBD-2 peptides, which are present in the transmembrane envelope glycoprotein of HIV-1 and HIV-2, and which contain the HIV-specific caveolin-binding motif, WXXXXWXXW (SEQ ID No. 1), where W is the aromatic amino acid tryptophan, and less frequently other aromatic acids such as phenylalanine or tyrosine, whereas X is a non-aromatic amino acid.

Antibodies raised against the CBD-1 epitope and the C-20 epitope were shown in the following examples to inhibit the HIV infection at early and late events in the HIV infectious cycle.

More specifically, the present invention provides a pharmaceutical composition comprising a caveolin-binding motif which is specific for HIV comprising one of the following peptide sequences:

WXXXXWXXW          (SEQ ID No. 1)

where W is tryptophan or an aromatic amino acid and X is any amino acid that is not aromatic or a pharmaceutically acceptable salt of said peptide sequence or a variant of SEQ ID No. 1 provided that said variant immunologically reacts with antibodies raised against the CBD-1 or CBD-2 peptides; and a pharmaceutically acceptable vehicle.

It should be noted that the three tryptophan (W) aromatic residues are found at specific amino acid positions in SEQ ID No. 1; i.e., at amino acid number 1, 6 and 9.

The pharmaceutical compositions or compositions of the present invention can be used to treat HIV-infection and are administered to mammals that are already sero-positive.

In another aspect, the present invention provides a vaccine comprising a caveolin-binding motif which is specific for HIV said vaccine comprising one of the following peptide sequences, WXXXXWXXW          (SEQ ID No. 1)

wherein W is tryptophan or an aromatic amino acid and X is any amino acid that is not aromatic or a pharmaceutically acceptable salt of said peptide sequence or a variant of SEQ ID No. 1 provided that said variant immunologically reacts with antibodies raised against the CBD-1 or CBD-2 peptides; and a pharmaceutically acceptable vehicle.

The vaccines of the present invention provide protection against HIV infection.

In another aspect the present invention provides a vaccine or a pharmaceutical composition said vaccine or pharmaceutical composition comprising an antigenic peptide CBD-1 (SEQ ID No. 2) and CBD-2 (SEQ ID No. 3) or variants of CBD-1 and CBD-2 (SEQ ID Nos. 4, 5, 6, or 7) or pharmaceutically acceptable salts of SEQ ID Nos. 2 to 7 and a pharmaceutically acceptable vehicle.

In another aspect the present invention provides a vaccine or a pharmaceutical composition said vaccine or pharmaceutical composition comprising an antigenic peptide of SEQ ID Nos. 8 or 9 or variants of SEQ ID Nos. 8 or 9 or pharmaceutically acceptable salts of SEQ ID Nos. 8 or 9 and a pharmaceutically acceptable vehicle.

In yet another aspect the present invention provides a vaccine or a pharmaceutical composition said vaccine or pharmaceutical composition comprising an antigenic peptide C-20 (SEQ ID No. 10) or variants of C-20 or pharmaceutically acceptable salts of C-20 or variants of C-20 and a pharmaceutically acceptable vehicle.

The antigenic peptides of the present invention, for example, at least SEQ ID Nos. 1 to 18, as well as their salt forms are the active ingredients in the vaccine and pharmaceutical compositions.

Pharmaceutically acceptable salts of the peptides of the present invention include acid salts (formed with free amino groups of the peptide), those formed with inorganic salts such as phosphoric acid or hydrochloric acid, those formed with organic salts such as acetic acid or oxalic acid and the salts formed with free carboxyl groups.

Any pharmaceutically acceptable vehicle can be used in the vaccine or pharmaceutical composition such as saline, dextrose glycerol, water, ethanol and the like and combinations thereof.

In addition buffering agents and adjuvants can comprise part of the vaccine or pharmaceutical composition formulation. Various adjuvants that are known in the art that can be used in the vaccine or pharmaceutical formulations include Complete Freund's Adjuvant (CFA), Incomplete Freund's Adjuvant (IFA), motanide ISA (incomplete seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, immuno-stimulating complexes such as Quil A, QS-21 and the like. Still other adjuvants are CpG oligonucleotides and double stranded RNA molecules, such as poly(A).poly(U). Combinations of the above adjuvants also encompass part of the vaccine or pharmaceutical compositions of the present invention.

These vaccine and pharmaceutical compositions can be prepared as exemplified in U.S. Pat. Nos. 6,514,942, 4,608, 251, 4,599,230 and 4,578,770 and in European Patent Application number 1201250.

The present invention also encompasses encapsulation of the peptides or antigens, their variants, as well as the adjuvants and pharmaceutically acceptable salts. In this regard any of the antigens of SEQ ID Nos. 1 to 18 can, for example, be combined with an adjuvant such as alum and a pharmaceutically acceptable carrier which mixture is then encapsulated.

For oral and mucosal vaccines and pharmaceutical compositions the antigen or their variants and the pharmaceutically acceptable vehicle or the mixture of the antigen or their variants, the adjuvant and the pharmaceutically acceptable vehicle are encapsulated with a polymer capsule of lactic acid and glycolic acid (poly LG).

In another aspect the capsules that are produced are designed to release the active ingredient in the vaccine in controlled phases thus eliminating the need for booster immunizations. In this regard, conventional encapsulation techniques for controlled release of active ingredients, which are encapsulated via polymers, are well known in the art.

Liposome and micelle encapsulation of the active ingredients of the pharmaceutical compositions and the vaccines described above, as well as ISCOMS (Immune Stimulating Complexes) can also serve as vehicles for antigen delivery.

Besides being encapsulated, the vaccines of the present invention can also be injected intramuscularly, subcutaneously or intravenously. Oral vaccine compositions are also contemplated. For oral compositions, the nucleic acid encoding the antigenic peptides described herein can be placed in an adenoviral vector under the control of an appropriate promoter and can be administered orally. In this regard, a mammalian promoter is desired for oral delivery to mammals.

The vaccines and pharmaceutical compositions of the present invention are administered in amounts that will be therapeutically effective and immunogenic and as known in the art, the dosage that is administered depends on the individual to be treated. Generally suitable dosages range on the order of 1 to 20 mg of active ingredient. Usually, when administered subcutaneously or intramuscularly multiple dosages of vaccine are administered at 7 to 15 days intervals over a period of two months.

With respect to the pharmaceutical compositions, these are also administered in a dosage range on the order of 1 to 20 mg of active ingredient administered subcutaneously or intramuscularly multiple dosages of vaccine are administered at 7 to 15 days interval over a period of two months. For the pharmaceutical compositions, the patient's viral load and CD4 counts are monitored during administration of the pharmaceutical composition.

In yet another aspect the present invention provides a composition comprising at least one of the peptides of SEQ ID Nos. 2 to 9 or a peptide variant of SEQ ID No. 1 as described herein. It will be appreciated that variants having 90% to 99.9999% sequence homology of the peptides of SEQ ID Nos. 1 to 9 are also included in the compositions. Moreover, as described above, these peptides can be glycosylated, have two cysteine residues introduced therein to form a disulfide bridge or can be phosphorylated. The peptides in this composition can also have linker sequences attached to their N- or C-terminals, which linker sequences can be fatty acids.

In another aspect the present invention provides peptides that inhibit HIV production said peptides comprise one of the following amino acid sequences:

(SEQ ID NO. 2)
L-E-Q-I-W-N-N-M-T-W-M-Q-W-D-K (SEQ ID NO. 3)
L-T-P-D-W-N-N-M-T-W-Q-E-W-E-R

-continued

```
                                                 (SEQ ID NO. 4)
C-T-T-A-V-P-W-N-A-S-W-S-N-K-S-L-E-Q-I-W-N-N-M-T-W-
Q-W-D-K (SEQ ID NO. 5)
C-H-T-T-V-P-W-P-N-D-S-L-T-P-D-W-N-N-M-T-W-M-Q-W-D-
K (SEQ ID NO. 6)
C-H-T-T-V-P-W-P-N-D-S-L-T-P-D-W-N-N-M-T-W-Q-E-W-E-
R (SEQ ID NO. 7)
C-T-T-A-V-P-W-N-A-S-W-S-N-K-S-L-E-Q-I-W-N-N-M-T-W-
Q-E-W-E-R (SEQ ID No. 8)
W-N-N-M-T-W-M-E-W (SEQ ID No. 9)
W-N-N-M-T-W-Q-Q-W (SEQ ID NO. 10)
D-G-I-W-K-A-S-F-T-T-F-T-V-T-K-Y-W-F-Y-R
```

Variants of these peptides such as deletions, additions or substitutions of amino acids in the peptides of SEQ ID Nos. 1 to 10 are also encompassed by the present invention and can be obtained by methods known in the art such as by site directed mutagenesis or by chemical synthesis, as long as these variants can immunologically react with antibodies raised against SEQ ID Nos. 1 to 10.

Examples of variants of SEQ ID NOs. 1 to 10 and encompassed by the present invention can be obtained as follows: For example, the amino acid sequence specificities of the synthetic peptide CBD-1 (designed after the consensus amino acid sequence of HIV-1), for use against HIV infection is the following: CBD-1 is composed of 15 amino acid residues and each amino acid is placed at a specific position (as shown below).

| 1 - L | (leucine) |
| 2 - E | (glutamate) |
| 3 - Q | (glutamine) |
| 4 - I | (isoleucine) |
| 5 - W | (tryptophan) |
| 6 - N | (asparagine) |
| 7 - N | (asparagine) |
| 8 - M | (methionine) |
| 9 - T | (threonine) |
| 10 - W | (tryptophan) |
| 11 - M | (methionine) |
| 12 - Q | (glutamine) |
| 13 - W | (tryptophan) |
| 14 - D | (aspartate) |
| 15 - K | (lysine) |

The 3 tryptophan (W) residues at amino acid positions 1, 6 and 9 in the caveolin-binding motif WXXXWXXW are conserved in all HIV strains. Therefore the CBD-1 sequence should contain 3 tryptophan residues placed at positions 5, 10, and 13, respectively. As a variation of this motif, the 3 tryptophan residues can be changed to phenylalanine or to tyrosine.

The isoleucine at 4 preceding W5 and threonine at position 9 preceding W10 are conserved by more than 97% among HIV-1 isolates. Therefore the CBD-1 peptide should contain I and T at position 4 and 9, respectively.

The asparagine at position 7 is conserved by more than 97%. Therefore the CBD-1 peptide should contain an asparagine at position 7. This asparagine represents a potential N-linked glycosylation site in gp41.

The methionine at position 8 is conserved in all but in HIV-1 O type this methionine is replaced by leucine. Thus, for immunization against HIV-1 O type the CBD-1 peptide can be modified slightly in order to contain leucine at position 8.

L1 can be replaced by Q, Y (tyrosine) or D.

E2 can be replaced by D or N.

Q3 can be replaced by E, D or S.

N6 can be replaced by D, E or Q.

M11 can be replaced by I, Q or L.

Q12, D14, and K15 are semiconserved. Thus, they can be replaced, for example, by E12, E14, and R15 or Q15, respectively.

In another example, the amino acid sequence specificities of the synthetic peptide CBD-2 (designed after the consensus amino acid sequence of HIV-2), for use against HIV infection is the following: CBD-2 is composed of 15 amino acid residues and each amino acid is placed at a specific position (as shown below).

| 1 - L | (leucine) |
| 2 - T | (threonine) |
| 3 - P | (proline) |
| 4 - D | (aspartate) |
| 5 - W | (tryptophan) |
| 6 - N | (asparagine) |
| 7 - N | (asparagine) |
| 8 - M | (methionine) |
| 9 - T | (threonine) |
| 10 - W | (tryptophan) |
| 11 - Q | (glutamine) |
| 12 - E | (glutamine) |
| 13 - W | (tryptophan) |
| 14 - E | (glutamate) |
| 15 - R | (arginine) |

The 3 tryptophan (W) residues in the caveolin-binding motif WXXXWXXW are conserved in all HIV strains. Therefore the CBD-2 sequence should contain 3 tryptophan residues placed at positions 5, 10, and 13, respectively. As a variation of this motif, the 3 tryptophan residues can be changed to phenylalanine or to tyrosine.

The amino acid residue at position 3, 7, 8, 9, 11 and 14 should be praline, asparagine methionine, threonine, glutamine, and glutamate, respectively.

L1 can be replaced by M.

T2 can be replaced by N, Q, or V.

D4 can be replaced by E.

N6 can be replaced by D, E or Q.

N7 in principal should be conserved as it represents a potential N-linked glycosylation site in gp41.

E12 can be replaced by Q.

R15 can be replaced by K, E, or Q.

In yet another example, a variant of SEQ ID NO. 1, SEQ ID NO. 2, SEQ ID NO. 3, SEQ ID NO. 4, SEQ ID NO. 5, SEQ ID NO. 6, SEQ ID No. 7, SEQ ID No. 8, SEQ ID No. 9 or SEQ ID No. 10 can have an extended sequence having additional amino acids at its N-terminal or C-terminal. These additional amino acids that are added to either terminal end can comprise between 1 and 20 amino acids. It will be appreciated that the addition of amino acids to SEQ ID NO. 1, SEQ ID NO. 2, SEQ ID NO. 3, SEQ ID NO. 4, SEQ ID NO. 5, SEQ ID NO. 6, SEQ ID No. 7, SEQ ID No. 8, SEQ ID No. 9 or SEQ ID No. 10 will not alter the antigen in such a way that it cannot immunologically react with antibodies raised against SEQ ID Nos. 1 to 10. Thus it is foreseen by the present invention antigens comprising the following antigens comprising amino acids sequences:

$X_n$-L-E-Q-I-W-N-N-M-T-W-M-Q-W-D-K-$X_m$ (SEQ ID NO. 11) where X is any amino acid, n is 0 to 20 and m is 0 to 20.

$X_n$-L-T-P-D-W-N-N-M-T-W-Q-E-W-E-R-$X_m$ (SEQ ID NO. 12) where X is any amino acid, n is 0 to 20 and m is 0 to 20.

Also embodied by the present invention are deletions of amino acids in SEQ ID NOs. 2 to 10 provided that peptides generated contain the HIV-specific caveolin-binding motif (CBM), and consequently antigens obtained from such deletions can immunologically react with antibodies raised against these sequences (SEQ ID Nos. 2 to 10).

Generally 1 to 5 amino acid deletions from each of SEQ ID NOs. 2 to 10 provided that the antigens having such deletions can immunologically react with antibodies raised against these sequences. For example, 4 amino acids can be deleted at the NH$_2$-terminal end and 1 to 2 amino acids sequences can be deleted from the COOH-terminal end of SEQ ID Nos. 2 to 10.

Antigens having amino acids substitutions in SEQ ID NOs. 2 to 10 are part of the present invention provided that the antigens with such substitutions can immunologically react with antibodies raised against these sequences (SEQ ID Nos. 2 to 10). One type of substitution is a conservative substitution i.e., a substitution of a residue by an another residue belonging to the same chemical group (aliphatic, aromatic, non-polar, polar, ionizable, H-bonding, basic, acidic, cyclic and sulfur-containing). For example, 4 substitutions can occur at the NH$_2$-terminal end, 1 or 2 substitutions at the COOH-terminal end and 5 substitutions in the interior of SEQ ID Nos. 2 to 10. Thus, antigens having the following amino acid sequences form part of the present invention:

```
                                          (SEQ ID NO. 13)
L-E-Q-I-X-N-N-M-T-X-M-Q-X-D-K where X = W, F, or Y (SEQ ID NO. 14)
L-T-P-D-X-N-N-M-T-X-Q-E-X-E-R where X = W, F, or
Y.
```

Substitutions can also occur in "N-X-S/T" (where X is any amino acid but not P) motifs for N-glycosylation contained in the antigens of SEQ ID Nos. 1 to 10. For example, in the CBD-1 and CBD-2 peptides where the motif of N-15 glycosylation is N7-M8-T9, the asparagine at position 7 can be replaced by any other amino acid or the threonine at position 9 can be replaced by any other amino acid except serine. Thus, antigens having the following amino acid sequences form part of the present invention:

```
                                           (SEQ ID NO 15)
L-E-Q-I-W-N-X-M-T-W-M-Q-W-D-K where X = A, G, V,
L, I, F, W, Y, M, C, S, T, Q, D, E, K, R, H or P (SEQ ID NO 16)
L-E-Q-I-W-N-N-M-X-W-M-Q-W-D-K where X = A, G, V,
L, I, F, W, Y, M, C, Q, D, E, K, R, H or P (SEQ ID NO 17)
L-T-P-D-W-N-X-M-T-W-Q-E-W-E-R where X = A, G, V,
L, I, F, W, Y, M, C, S, T, Q, D, E, K, R, H or P (SEQ ID NO 18)
L-T-P-D-W-N-N-M-X-W-Q-E-W-E-R where X = A, G, V,
L, I, F, W, Y, M, C, Q, D, E, K, R, H or P
```

Also encompassed by the present invention are peptides having 90% to 99.9999% sequence identity to SEQ ID NOs. 1 to 10, with the proviso that such antigens can immunologically react with antibodies raised against these sequences (SEQ ID Nos. 1 to 10).

Variants of the peptides of SEQ ID Nos. 1 to 10 can be assayed to determine whether they can combine with antibodies directed against the peptides of SEQ ID Nos. 1 to 18 using typical immunoassays such as sandwich assays, ELISA assays and the like. The antibodies against the peptide of SEQ ID Nos. 1 to 18 can be generated by conventional methods in the art as set forth below and as illustrated in the Examples.

The above mentioned peptides and variants of these peptides can have a modified peptide bond in the —CONH— peptide bond is modified and replaced by a (CH$_2$NH) reduced bond, a (NHCO) retro-inverso bond, a (CH$_2$—O) methyleneoxy bond, a (CH$_2$—S) thiomethylene bond, a (CH$_2$CH$_2$) carba bond, a (CO—CH$_2$) cetomethylene bond, a (CHOH—CH$_2$) hydroxyethylene bond), a (N—N) bond, a E-alcene bond or also a —CH=CH— bond.

Still, the above mentioned peptides and variants of these peptides can be additionally modified by side-chain oxidation such as the introduction of two cysteine residues to form a disulfide bridge or phosphorylation. A disulfide bridge may be formed by introducing two cysteine residues either at the extremities of the antigen or at internal positions inside the amino acid sequence or at one extremity and one internal position. If necessary, the modification can also include glycosylation.

Linker sequences can also be introduced into the extremities (the N- and/or C-terminals) of the peptides and variants of these peptides, which linker sequences may comprise a molecule such as biotin or fatty acids. For example, fatty acids such as myristic acid or palmitic acid are linked by amide or aryl ester bonds directly to the C-terminal end of the last amino acid of SEQ ID Nos. 1 to 18 or their variants.

Furthermore, the peptides or the antigens or their variants of the invention can be associated covalently or non-covalently with peptides corresponding to the V3 loop and/or any HIV-1 or HIV-2 envelope protein or glycoprotein or/and a foreign antigen of interest such as HBs (surface antigen of the hepatitis B virus) as described in U.S. Pat. No. 5,314,808 or LSA3 antigen from *Plasmodium falciparum* as described in U.S. Pat. No. 6,191,270. In this regard, the present invention also includes mixtures of the peptides or antigens of the present invention with other antigens known in the art. These mixtures or the covalently bound antigens of the present invention can be used in pharmaceutical compositions and in vaccines.

All of the above peptides may be synthesized by any conventional chemical method including, but not limited to, Fmoc chemical synthesis, Boc chemical synthesis and the conventional method described by Merrifield and as described by Neimark and Briand, 1993; King et al., 1990 (30, 31). Peptide synthesis in Fmoc or Boc chemistry, can be realised by using a multichannel peptide synthesizer as the ABI 433A Peptide Synthesizer or the Pioneer Peptide Synthesizer, both commercialized by Applied Biosystems. By using conventional methods large quantities of the antigens can be generated with a high degree of purity and at relatively low costs. These peptides have very little contamination, are easy to sterilize, store and ship.

In another aspect the peptides of the present invention may be produced by recombinant technology as the result of expression of nucleic acids encoding all of the above peptides and their variants. Thus, the nucleic acid sequences described herein, in case of DNA, are introduced into vectors using conventional recombinant technology and can be placed under the control of a promoter which expresses the nucleic acid insert in various cells such as bacteria, yeast and mammalian cells. The antigen produced is then further purified by known methods.

When the vector is under the control of a mammalian promoter, the vector is a source of a naked DNA vaccine. Thus, the present invention relates to a plasmid containing the DNA encoding the immunogenic antigens of SEQ ID Nos. 1 to 18. These plasmids can be directly injected into muscle cells or attached to gold particles that can be bombarded into the tissue. The direct injection of the naked DNA vaccine of the present invention results in the DNA being taken up by the muscle cells and the encoded protein antigens of SEQ ID Nos. 1 to 18 are expressed thereby eliciting a protective immune response against HIV infection.

The naked DNA which is injected into muscle cells can be via a gene gun, using complexed DNAs, by electroporation, via bacterial systems or via viral delivery. These methods are well known to the person skilled in the art.

Therefore, the present invention also relates to combinations of nucleic acids that encode CBD-1, CBD-2, CBM-1/TH-1, CBM-1/TH-2, CBM-2/TH-1, CBM-2/TH-2 or C-20 peptides or their variants. For an example, the nucleic acid sequence encoding the CBD-1 peptide (L-E-Q-I-W-N-N-M-T-W-MQ-W-D-K) (SEQ ID No. 2) can be one of the following nucleic acids combinations:

A-B-C-D-TGG-E-F-ATG-G-TGG-ATG-H-TGG-I-J wherein A is selected from TTA, TTG, CU, CTC, CTA and CTG; B is GAA or GAG; C is CAA or CAG; D is ATT, ATC or ATA; E is AAT or AAC; F is AAT or AAC; G is ACT, ACC, ACA or ACG; H is CAA or CAG; I is GAT or GAC: and J is AAA or AAG To illustrate the 9216 potential nucleic acid combinations encoding the CBD-1 peptide, a few are given below:

```
                                              (SEQ ID Nos. 19)
5'- CTG GAG CAG ATC TGG AAC AAC ATG ACC TGG ATG
CAG TGG GAC AAG -3'

(SEQ ID Nos. 20)
5'- CTG GAA CAG ATT TGG AAT AAC ATG ACC TGG ATG
GAG TGG GAC AGA -3'

(SEQ ID Nos. 21)
5'- CTG GAA CAG ATT TGG AAT AAC ATG ACC TGG ATG
CAG TGG GAC AAA -3'
```

A person skilled in the art can easily ascertain and produce the other 9,213 nucleic acids by using conventional techniques in the art.

The nucleic acid sequence encoding the other peptides of the invention can be obtained routinely by using computer programs that back translate a protein sequence as the program backtranseq developed by Alan Bleasby (ableasby @ hgmp.mrc.ac.uk) HGMP-RC, Genome Campus, Hinxton, Cambridge CB10 1SB, UK.

Any nucleic acids hybridizing under stringent conditions with nucleic acids encoding at least one of the peptides according to the invention is also embraced by the invention. As used herein, the term "stringent conditions" refers to conditions which permit hybridization between the probe sequences and the nucleotide sequence to be detected. Suitable stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. The temperature range corresponding to a particular level of stringency can be further narrowed by calculating the purine to pyrimidine ratio of the nucleic acid of interest and adjusting the temperature accordingly. Variations on the above ranges and conditions are well known in the art.

In another aspect, the present invention encompasses antibodies raised against any of the antigens or antigen variants described herein which recognizes specifically the immunogenic antigens of SEQ ID Nos. 1 to 18.

The antibodies provided by the present invention include monoclonal antibodies, polyclonal antibodies, oligoclonal antibodies and antibodies with a restricted specificity.

The monoclonal antibodies can be produced by classical methods such as those described by Kohler and Milstein (1975) or using the procedures described in Sambrook et al, *A Guide to Molecular Cloning, A Laboratory Manual*, $2^{nd}$ edition (1989) using the antigens or antigens variants described above. More specifically the antigens that are used to obtain the antibodies are those antigens of SEQ ID Nos. 1 to 18.

Polyclonal, oligoclonal or antibodies with a restricted specificity can be prepared according to conventional methods such as those described in Sambrook, supra using the antigens or antigen variants described above. More specifically the antigens that are used to obtain the antibodies are those antigens of SEQ ID Nos. 1 to 18.

The present invention also relates to the use of monoclonal antibodies, polyclonal antibodies, oligoclonal antibodies and antibodies with a restricted specificity in an assay to detect HIV infection. Thus, the present infection also relates to a method for detecting the presence of HIV in a biological sample, comprising contacting the biological sample taken from a mammal with an antibody specifically directed against HIV under conditions that allow the formation of an immunological complex; and detecting the immunological complex that is formed.

The biological sample can be sera, urine, saliva, biopsy material and the like.

The design of immunoassays is conventional in the art and protocols such as the use of solid supports or immunoprecipitation are well known techniques. The antibody can be labeled for detection purposes using enzymatic, fluorescent, chemiluminescent, radioactive or dye labels. Assays that amplify the signals from the immune complex such as assays using biotin and avidin or streptavidin and enzyme-linked immunoassays such as ELISA or sandwich assays are part of the present invention.

A kit containing the antibody specifically directed against HIV as well as reagents necessary for the immunological reaction is also encompassed by the present invention.

In yet another aspect, the present invention relates to the use of the antibodies specifically directed against HIV for immunotherapy to prevent HIV infection. In this aspect of the invention the antibodies specifically directed against HIV include monoclonal antibodies, polyclonal antibodies and oligoclonal antibodies. Once the antibodies are prepared by conventional methods known in the art, they are further purified and are administered with a pharmaceutically acceptable vehicle. The purified antibodies may also be encapsulated using the conventional methods described above. Furthermore, the antibodies can be complexed to a solid particulate matrix and administered as a solid-matrix-antibody-antigen complex (SMAA).

In another aspect, the present invention provides neutralizing antibodies capable of inhibiting HIV infection, which can be used in passive vaccine compositions. These neutralizing antibodies are directed against the CBD-1/CBD-2 or C-20 epitopes. More specifically the peptides or antigens that are used to obtain the neutralizing antibodies are those peptides or antigens of SEQ ID Nos. 1 to 18.

In order to assay for a potent neutralizing response of the antibodies conventional assays are known such as those set forth in the Examples, as well as MAGI (multinuclear activation of galactosidase indicator), SMAGI for SIV or the typical neutralization assay of premixing virus sample and antibody sample, using this mixture to inoculate a cell line and measuring after cultivation the p24 viral replication or reverse transcriptase. Monoclonal neutralizing antibodies can be obtained by conventional methods as described, for example, in Huls et al. (63) and Gauduin et al. (64).

The present invention also provides for the use of the peptides or the antigens or the antibodies described herein to treat or prevent HIV infection. Thus, the present invention provides a method to treat or prevent HIV infection by administering to a mammal in need of such treatment a pharmaceutically acceptable amount of the vaccine or the pharmaceutical composition of the present invention. The pharmaceutical composition or the vaccine includes all of the peptides or antigens described herein and their variants including the peptides of SEQ ID Nos. 1 to 18 or the antibodies which recognize specifically the antigens of SEQ ID Nos. 1 to 18 or neutralizing antibodies.

Also encompassed by the present invention is the use of the peptides of SEQ ID Nos. 1 to 18 or the antibodies, which recognize specifically the peptides of SEQ ID Nos. 1 to 18 or neutralizing antibodies for the preparation of a medication to treat or prevent HIV.

A method to treat or prevent HIV entry into the cell and budding from the cell is encompassed by the present invention said method comprising administering a pharmaceutically acceptable amount of the peptides of SEQ ID Nos. 1 to 18 or the antibodies which recognize specifically the peptides of SEQ ID Nos. 1 to 18 described herein or neutralizing antibodies. Thus, the present invention encompasses use of the antigens of SEQ ID Nos. 1 to 18 or the antibodies, which recognize specifically the antigens of SEQ ID Nos. 1 to 18 described herein or neutralizing antibodies to treat or prevent the infectious cycle of HIV.

In yet another aspect the present invention encompasses the use of the antigenic peptides of SEQ ID Nos. 1 to 9 and 11 to 18 in an immunological assay such as an ELISA assay to measure the presence of neutralizing antibodies in mammals having HIV in long term survivors. Long term survivors are those mammals which are sero-positive for HIV but do not have the full blown illness of AIDS. In this aspect a diminution of the amount of neutralizing antibody is indicative of a change to acute illness.

In another aspect the present invention relates to a method of isolating anti-HIV molecules, this method comprises attaching the peptidic antigens of SEQ ID Nos. 1 to 18 and their variants to a solid support; incubating anti-HIV molecules with said attached antigen and eluting the anti-HIV molecules from the solid support thereby isolating said anti-HIV molecules.

In yet another aspect the present invention provides a method of selecting or isolating anti-HIV molecules comprising attaching at least one of the antigens of SEQ ID Nos 1 to 9 and 11 to 18 to a solid support; incubating with a caveolin preparation or with the C-20 peptide in the presence of anti-HIV molecules that prevent the interaction of caveolin with said attached antigens; and selecting or isolating said anti-HIV molecules.

In yet another aspect the present invention provides a purified peptide comprising at least one of the sequences of SEQ ID Nos. 1 to 18, as well as the use of the purified peptide comprising at least one of the sequences of SEQ ID Nos. 1 to 18, to isolate anti-I-HIV molecules.

Finally the present invention provides the use of a complex of caveolin bound to the peptides of SEQ ID Nos. 1 to 9 and 11 to 18 to prevent HIV infection. In this regard, the caveolin bound to the peptide sequences provides a pharmaceutical composition that can be administered as a medicament to prevent HIV infection.

In order to fully illustrate the present invention and advantages thereof, the following specific examples are given, it being understood that the same are intended only as illustrative and in nowise limitative.

EXAMPLES

Example 1

Analysis of the Amino Acid Sequence of the gp41 Ectodomain, in the Caveolin-Binding Domain 1 Among HIV-1, HIV-2 & SIV Isolates Analysis of the amino acid sequence of the gp41 ectodomain (amino acids 512 to 681) of 862 HIV-1 isolates from HIV clades, including A, B, C, D, E, F, G, H, I, J and Q clades, has constituted a consensus sequence of the ectodomain with the highest frequency emerging on each position (1). This analysis pointed out that the tryptophan residues in the consensus caveolin-binding motif, WNNMTWMEW, (SEQ ID No. 8) are conserved among all 862 HIV-1 isolates, Furthermore, the other amino acids in this motif are conserved 90-97% (FIG. 4).

This caveolin-binding motif, WXXXXWXXW (SEQ ID No. 7) was also conserved among various HIV-2 isolates and even in the corresponding domain in the case of the simian immunodeficiency virus (SIV) (FIG. 5). FIG. 5 shows an alignment of the consensus amino acid sequence in gp41 (amino acids 619 to 633) containing the caveolin-binding domain 1 (deduced from (1)) with the corresponding sequences found in the X4 HIV-1 LAI, R5 HIV-1 Ba-L, X4 HIV-1 Eli, primary HIV-1 isolates HIV-1 92UG037 (syncytium inducing) and 92BRO25 (non-syncytium inducing), HIV-2 isolates ROD and EHO, SIV isolates agm and sm (39) and the synthetic peptide CBD-1 peptide. The conservation of the caveolin-binding motif among HIV-1, HIV-2 and SIV isolates reveals that there is a natural selective pressure to conserve this motif since it is essential for infection by these retroviruses.

Example 2

Synthesis of CBD-1 and Biotinylated CBD-1 Peptides

The CBD-1 peptide having the amino acid sequence corresponding to the caveolin-binding domain in the HIV-1 gp41 ectodomain, namely LEQIWNNMTWMQWDK (amino acids 619-633) (SEQ ID No. 1) was synthesized in Fmoc chemistry by the stepwise solid-phase methodology using a multichannel peptide synthesizer. Protected amino acids were coupled by in situ activation with (benzotriazol-1-yloxy)tris-(dimethylamino)phosphonium hexafluorophosphate and Nα-Fmoc deprotection was performed as previously described (30). For the synthesis of the biotinylated CBD-1, a biotinyl moiety was coupled on the resin at the N terminus of the peptide after the last deproptection step of the peptide chain. At the end of the synthesis, side chain deprotection and cleavage of peptides from the solid support were performed by treatment with reagent K (82.5% TFA, 5% phenol, 5% water, 5% thioanisole, 2.5% 1.2-ethanedithiol) for 2.5 hours at 20° C. (31). Peptides were purified by reverse-phase HPLC (RP-HPLC) using a Perkin-Elmer preparative HPLC system on an Aquapore ODS 20 mm column (100×10 mm). The elution was achieved with a linear gradient of aqueous 0.1% TFA (A) and 0.08% TFA in 80% acetonitrile, 20% water (B) at a flow rate of 6 ml/min with UV detection at 220 nm. Homogeneity of the peptides was assessed by RP-HPLC on a Beckman instrument (Gagny, France) with a Nucleosil C18 5 mm column (150×4.6 mm) using a linear gradient of 0.1% TFA in water and acetonitrile containing 0.08% TFA at a flow rate of 1.2 ml/min. All peptides were identified by matrix-assisted laser desorption and ionization time-of-flight (MALDI-Tof) spectra on a Protein TOF™ mass spectrometer (Bruker, Wissembourg, France).

Example 3

HIV Induced Aggregation of Caveolin-1 in MT4 Cells as Revealed by Laser Scanning Confocal Immunofluorescence Microscopy MT 4 cells were incubated at 37° C. for 30 minutes in the absence (Control panels) or presence of HIV-1 LAI (HIV panels) before washing and further incubated at 20° C. for 60 minutes in the presence of anti-HIV-1 human serum (panel HIV-TR). After partial fixation with 0.25% PFA, cells were incubated at 20° C. for 45 minutes with rabbit anti-caveolin-1 antibody (Caveolin-FITC). Bound human antibodies were revealed by goat Texas Red (TR)-conjugated anti-human antibodies, while rabbit antibodies were revealed by FITC-conjugated goat anti-rabbit antibodies (Vector Laboratories Inc. CA). The experimental conditions were described previously (6).

The results are shown in FIG. 1. A cross-section for each staining is shown with the merge of the two colors in yellow. The anti-HIV serum was specific to HIV-1 particles since the serum did not give a signal in uninfected cells under similar experimental conditions. In an immunoblot assay, the serum reacted strongly with HIV-1 envelope glycoproteins and Gag proteins.

The anti-caveolin antibody reacted with the 22 kDA caveolin protein in immunoblot assays using crude extracts from MT4 cells.

Example 4

Recovery of Caveolin in Detergent Insoluble Higher Density Fractions Containing also HIV-1 p24, p17 and gp41

Figure 2:
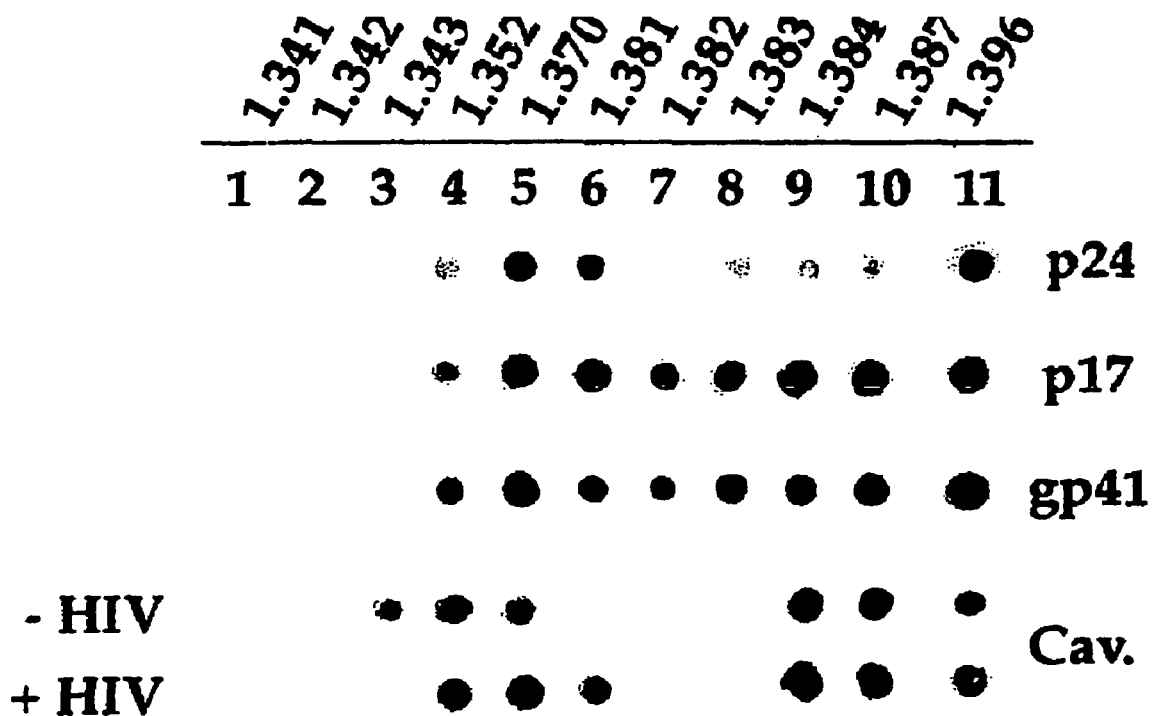
Figure 3:
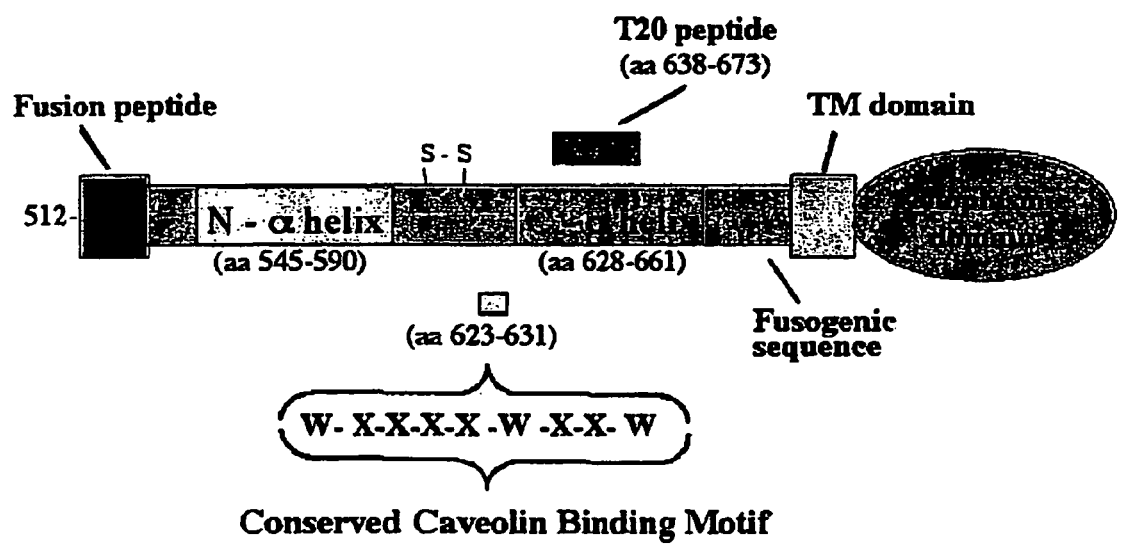

Uninfected (-HIV) and HIV-1 LAI infected (all other panels) MT4 cells were incubated for 4 hours at 37° C. before washing in PBS. Cells were then extracted in buffer containing 0.5% Triton X-100® and processed for analysis by equilibrium centrifugation on a discontinuous sucrose gradient as described before (6). The buoyant density of each fraction in g/ml is indicated at the top of each fraction. Fractions 3 to 6 correspond to GEM domains whereas fractions 9 to 11 correspond to Triton-soluble fractions from the plasma membrane and cytoplasmic proteins. Dot immunoblotting using antibodies against HIV matrix p17, capsid p24 and the transmembrane envelope glycoprotein gp41 and caveolin-1 was previously described (6). The results are shown in FIG. 2. This figure was prepared from scanned blots in Adobe Photshop.

Example 5

The Binding of Biotinylated CBD-1 to Caveolin in Crude Cell Extracts

MT4 cells were extracted in buffer containing 10 mM Hepes, pH 7.6, 50 mM KCl, 400 mM NaCl, 1 mM EDTA, protease inhibitor cocktail and 1% Triton X-100®. Extracts were centrifuged at 12,000×g and the supernatants were stored at 80° C. 100 µl of cell extracts were first diluted with 400 µl of homogenization buffer and left at 4° C. for 10 minutes before centrifuging at 12,000×g.

The diluted supernatants were then incubated at 4° C. in the presence of 0, 2, 5, 10 and 20 µM of the biotinylated CBD-1 peptide. After 90 minutes, 100 µl of avidine-sepharose were added in each sample and the samples were further incubated at 4° C. for 2 hours with gentle shaking. The samples were then washed extensively with PBS and proteins bound to avidine-sepharose were eluted in 100 µl of electrophoresis sample buffer containing SDS and analyzed by SDS-PAGE (using a 12.5% polyacrylamide gel) for immunoblotting with rabbit anti-caveolin 1 antibodies (INTERCHIM) as previously described (6).

Cell extracts were first incubated with 50 µM of CBD-1 (+) or without CBD-1 (−) before the addition of 10 µM biotinylated CBD-1 and further processed as above. Lane E represents the analysis of crude cell extracts diluted 1-fold in the electrophoresis sample buffer. The caveolin reacting antibodies were visualized with an enhanced chemiluminescence (ECL) reagent (Amersham Pharmacis Biotech) and by exposure to autoradiography film (Amersham Pharmacia Biotech). The results are set forth in FIG. 6. The position of the molecular markers is on the left.

Figure 6:
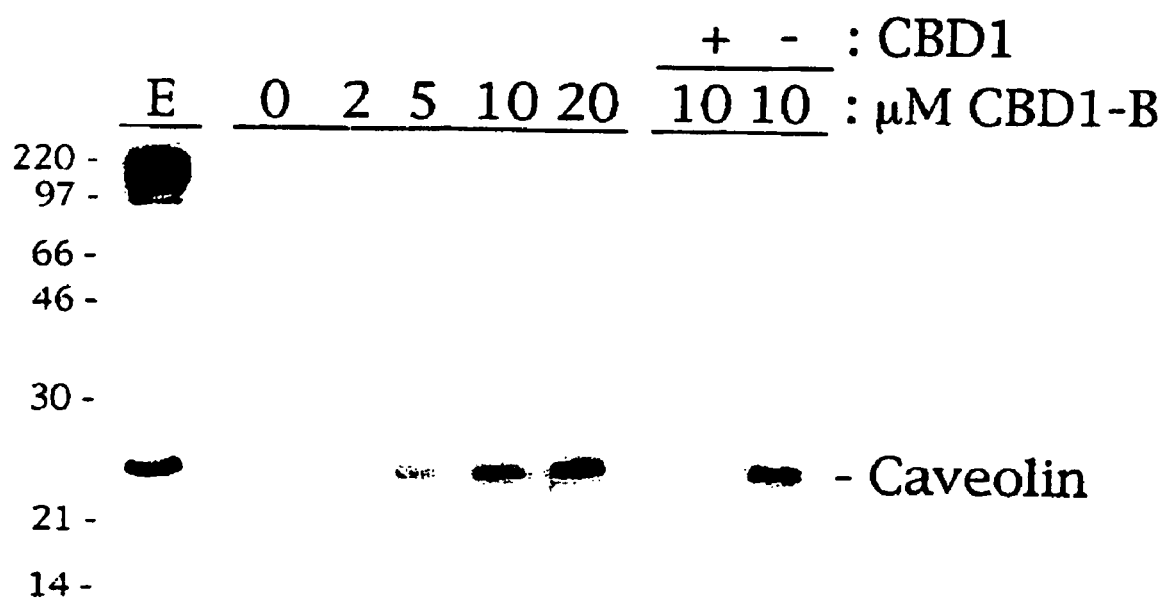

These results show that caveolin was purified from crude extracts in the presence of the biotinylated CBD-1, in a dose dependent manner, thus demonstrating that affinity of caveolin to bind CBD-1. This binding was specific as demonstrated by the reduced capacity of the biotinylated CBD-1 to bind caveolin in the presence of excess CBD-1 FIG. 6, lanes (+) and (−) CBD-1). It should be noted that only a small portion of monomeric caveolin was found to be solubilized by the extraction of cells in the buffer containing 1% Triton-X-100®. The strong signal at the top of the gel revealed by the anti-caveolin antibody in the crude extracts of the cells corresponds to oligomeric caveolin, which remains insoluble even in the presence of SDS (FIG. 6, lane E). Consequently, this high molecular insoluble caveolin complex does not bind the CBD-1 peptide.

Example 6

The CBD1 Peptide Becomes Internalized into Cells

Several studies in laser scanning confocal immunofluorescence microscopy were conducted to investigate the interaction of the CBD-1 peptide with cells and its effect on Midkine. Midkine is an anti-HIV cytokine that inhibits HIV infection by an autocrine and paracrine manner, by blocking the attachment of HIV to permissive cells (33). Midkine binds its low affinity receptor, surface-expressed nucleolin, before entry into cells by an active process in which lipid rafts appear to be implicated (34). It was demonstrated that the CBD-1 peptide blocks entry of Midkine into cells without affecting Midkine binding to cells.

On intact cells, the CBD-1 peptide appeared to interact with caveolin at the plasma membrane. Indeed, cross-linking of cell surface bound biotinylated CBD-1 peptide resulted in the coaggregation of CBD-1 with caveolin. Following binding to cells, the CBD-1 peptide entered cells in an active process, since entry was dependent on incubation temperature; i.e., CBD-1 entry occurred at 37° C. but not at 20° C.

HeLa cells in culture medium were incubated (45 min at 37° C.) with the biotinylated CBD-1 peptide (5 µM). Cells were then washed and fixed with paraformaldehyde/Triton X-100 solution. The biotinylated CBD1 peptide associated in such fixed cells was revealed by rabbit anti-biotin antibodies (Enzo Diagnostics, Inc. N.Y.). The secondary antibody was Texas Red dye-conjugated donkey anti-rabbit IgG (Jackson ImmunoResearch Laboratories, PA). Confocal microscopy was performed as described previously (6). A scan of a cross section towards the middle of the cell monolayer showing the TR15 labeled CBD-1 localized in the cytoplasm and the corresponding phase contrast are presented (FIG. 7).

Example 7

The Production of Specific Anti-CBD-1 Antibodies in Rabbits

The biotinylated CBD-1 peptide was solubilized in water containing 10% DMSO at a concentration of 2 mg/ml. 100 µg of this solution (50 µl) was mixed with 50 µg of streptavidin in 250 µl of distilled water. This solution was then mixed with 250 µl of complete Freund's adjuvant (CFA) for the first injection and incomplete Freund's adjuvant (IFA) for the following injections. 10 ml of blood was collected from the rabbits before the first injection of antigen; this serum was referred to as S0 or pre-immune serum.

The rabbits (Fauves de Bourgogne) were injected intramuscularly with 500 µl of the antigen/adjuvant mixture. The following Table 1 presents the injection and bleeding dates of the rabbit named "Aldernay":

TABLE 1

| | Bleeding S0: day 0 |
|---|---|
| Injection 1: day 35 | |
| Injection 2: day 49 | Bleeding S1: day 63 |
| Injection 3: day 70 | Bleeding S2: day 77 |
| Injection 4: day 84 | Bleeding S3: day 91 |
| Injection 5: day 106 | Bleeding S4: day 112 |
| Injection 6: day 126 | Bleeding S5: day 133 |
| | Bleeding S6: day 153 |

All sera were tested by ELISA using 2 types of plates (PVC and Maxisorp) coated with the CBD-1 peptide. The optical density (OD) was measured at 450 nm. An OD value above 0.20 was considered positive.

Figure 8:
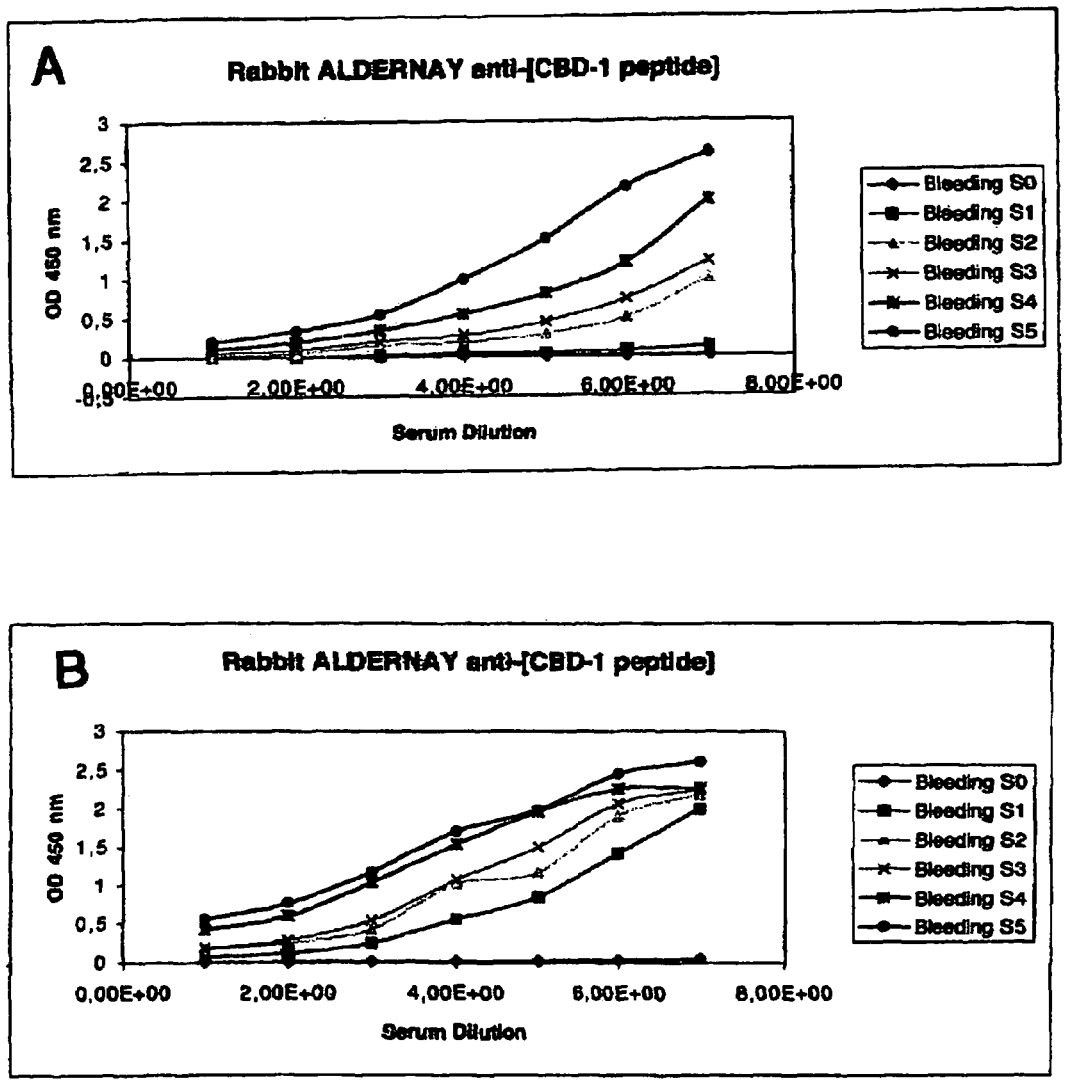

The results are presented in FIG. 8. After the first 3 injections, there was already a significant amount of antibodies against CBD-1 as observed at a dilution of 1/2,000. The production of anti-CBD-1 antibodies increased gradually with the number of injections.

These results indicate that the CBD-1 peptide is immunogenic.

Example 8

CBD-1 is an Immunogenic Peptide that Elicits a Protective Immune Response Against HIV Infection in the MT4 Lymphocytic Cell Line The anti-HIV action of antibodies was tested by using an HIV-1 LAI isolate on MT4 cells. Cells were infected with HIV by incubation at 37° C. for 90 minutes. The cell suspension was then centrifuged to remove the medium and the cells were incubated at 37° C. Cells were passaged every 2-3 days and a small aliquot of the culture supernatant was collected and the concentration of p24 by ELISA was then measured in such supernatants.

In some experiments, cells were also collected at different times post infection, washed in PBS and lysed in buffer containing Triton X-100®. Cell extracts were then analyzed by immunoblotting to investigate the steady state level of viral proteins. MT4 cells were cultured with 10% (v/v) heat inactivated (56° C., 30 minutes) fetal calf serum (FCS; Boehringer Mannheim GmbH, Germany) and 50 IU/ml Penicillin-Streptomycin (Gibco, BRL). The HIV-1 isolate was propagated and purified as previously described (32). The MOI of the HIV for different infections was 1. For the assay of HIV-1 LAI attachment, anchorage and colocalization studies, purified virus was used at MOI 3 (32).

The pre-immune serum (S0) and immune serum (S5) as indicated in Table 1 above, were tested against infection of MT4 cells with the HIV-1 LAI isolate. Virus infection was carried out in the presence of sera S0 and S5 at a 1/10 dilution. After 90 minutes of incubation with the virus, cells were centrifuged and suspended in fresh culture medium supplemented with sera S0 and S5 at a 1/10 dilution. Cells were passaged every 2-3 days by adding fresh culture medium. The rabbit sera were added once again on day 4.

Samples of the culture supernatants were collected at days 2, 4, 6 and 8 post-infection for the p24 ELISA. The results are presented in FIG. 9. Virus infection in cultures with the pre-immune serum S0 increased gradually reaching a peak at 6 days post-infection. HIV production measured by the concentration of p24 was significantly inhibited. The degree of inhibition was 85% and 75% at day 6 and 8 post-infection, respectively.

Figure 9:
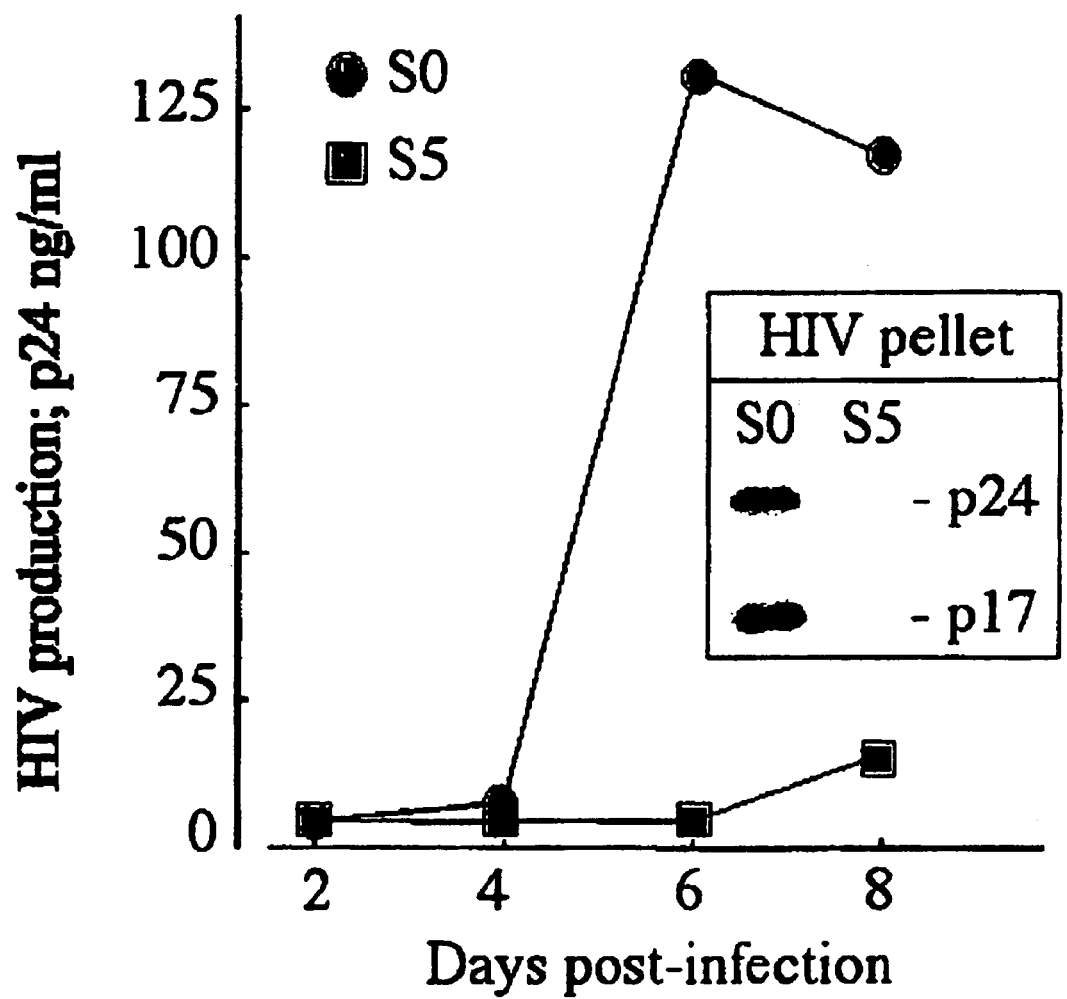

In order to confirm the inhibition of HIV production by the anti-CBD1 antibodies, the culture supernatant from S0 and S5 treated cells were collected on day 6 and were centrifuged at 100,000 g to pellet virus particles. The viral pellet was then analyzed by immunoblotting using antibodies specific for the HIV core p24 and matrix p17 (FIG. 9, the insert entitled HIV pellet). The presence of p24 and p17 were revealed in the HIV pellet recovered from the cultures treated with the preimmune S0 serum, whereas these proteins were hardly detectable in the corresponding sample obtained from cultures treated with the immune S5 serum.

These results indicated that anti-CBD-1 antibodies are neutralizing antibodies capable of blocking HIV infection.

Example 9

Addition of Anti-CBD-1 Antibodies at 2 Days Post-Infection Inhibits HIV Infection in a Dose Dependent Manner Without Affecting Cell Viability MT4 cells were infected with HIV-1 LAI and at 2 days post-infection, cells were suspended in fresh culture medium supplemented with a 1/10 dilution of the pre-immune S0 or the immune serum S5 at 1/10, 1/15, 1/20 and 1/40 dilutions from Aldernay. Cells were passaged on day 4 by adding one volume of fresh culture medium. Therefore, antisera were added only at day 2 post-infection. As a control for the inhibition of HIV infection, samples of cells were treated with AZT (0.1 and 0.5 μM), which was supplemented in the culture medium from day 0 to day 6. HIV infection was monitored by the p24 concentration in the culture supernatant and was inhibited by the immune S5 serum in a dose dependent manner (FIG. 10A). The 1/40 dilution of S5 resulted in 50% inhibition on virus production.

The inhibitory action of the anti-CBD-1 antibodies on HIV infection was not a consequence of a toxic effect on cells, since no apparent effect on cell viability was measured by the MTT (3-(4,5-dimethylthiazol-2-yl)-2,5-diphenyltetrazolium bromide) was observed (FIG. 10B).

HIV-1 infected MT4 cells were treated at 2 days post-infection with a 1/10 dilution of the pre-immune S0 (lanes P) or the immune S5 (lanes I) serum from Aldernay. In a parallel experiment, cells were infected without any treatment (lanes C) or treated with AZT (1 μM). At 6 days post-infection, culture supernatants were centrifuged at 100,000×g to pellet virus particles. Cell and HIV extracts were then analyzed by immunoblotting using human HIV positive serum (FIG. 11A) or the anti-p17 monoclonal antibody FIG. 11B. The position of the precursor Gag p55 and its cleaved products p40, p24 and p17 are shown to the right in FIG. 11.

Figure 11:
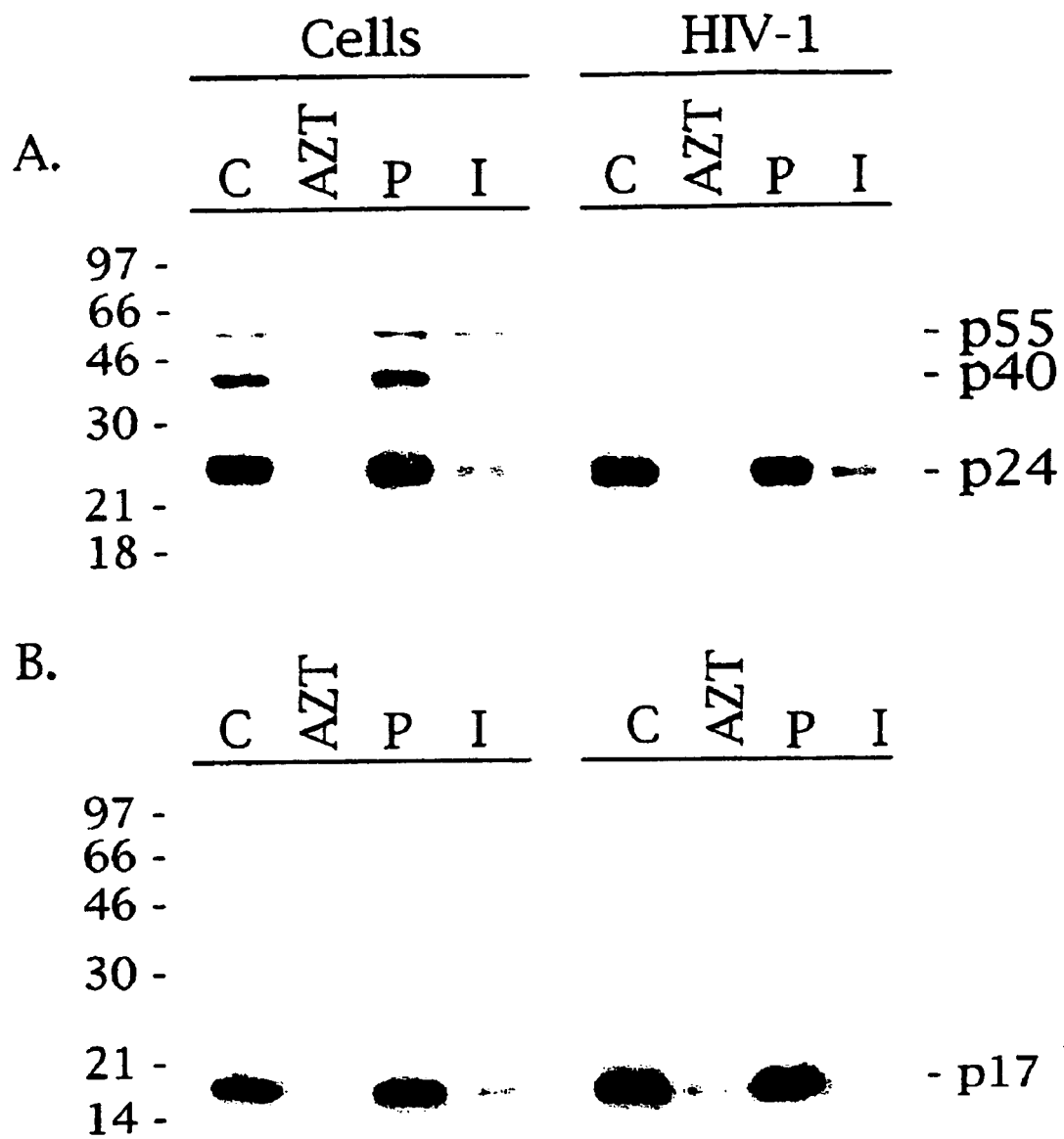

There was no significant difference in the virus production between untreated and S0 treated cells (FIG. 11, lanes C and P). However, there was a drastic inhibition of virus production in the cell culture treated with the anti-CBD-1 antibodies (FIG. 11, lane I). This confirmed that the addition of anti-CBD-1 antibodies at 2 days post-infection is still efficient for inhibition of HIV particle production.

Example 10

Anti-HIV Activity of the Rabbit Sera After Immunization with the CBD-1 Peptide

MT4 cells were incubated with HIV-1 LAI for 90 min at 37° C. before suspension of cells in fresh culture medium supplemented with the different rabbit sera fram Aldernay before (S0) and after each immunization (S1 to S5) was tested at 1/20 dilution. Cells were passaged on day 3 by the addition of 1 volume of fresh culture medium supplemented with the different sera. At 6 days post-infection, virus production was monitored by measuring the concentration of p24 by ELISA in culture supernatants and in cell extracts for free HIV and cell-associated HIV, respectively (FIG. 12).

Figure 12:
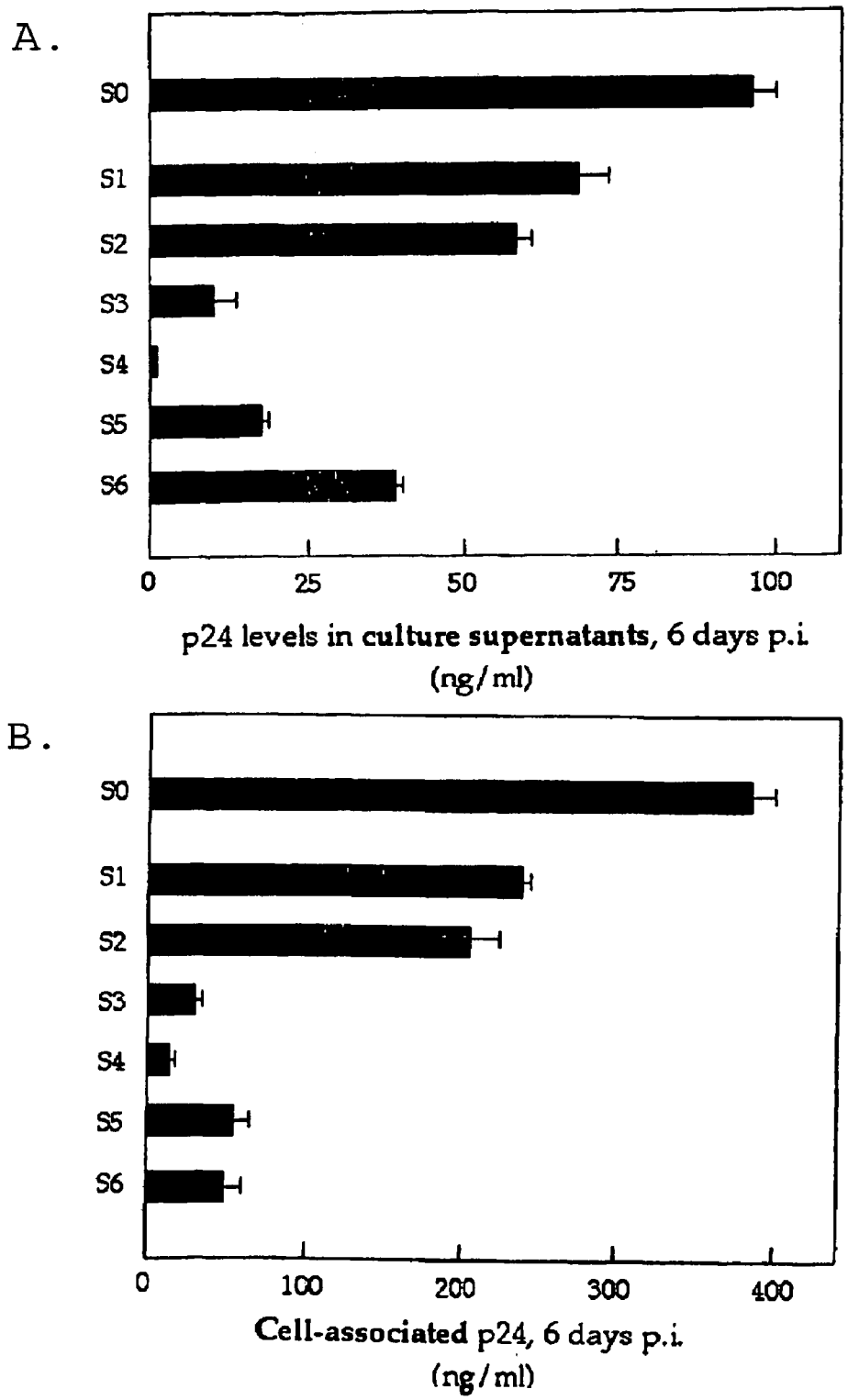

The anti-HIV activity developed gradually after each successive immunization with the CBDI peptide reaching to a very strong effect after the fourth immunization (FIG. 12, histograms S3). There was still a significant degree of anti-HIV activity 4 weeks after the last immunization with the CBD-1 peptide (FIG. 12, histogram S6).

The fact that HIV infection was inhibited drastically by the S3 and S4 serum albeit its addition after HIV binding to cells at 37° C., suggests that the CBD-1 epitope in gp41 should be accessible even following the conformational changes of the cell-bound gp120-gp41 complex.

The results presented in FIG. 12 show that the degree of inhibition of HIV infection by the rabbit Aldernay sera S3 and S4 is slightly higher than that of S5 and S6. These results point out that the number of administration of the CBD-1 peptide should not exceed five injections (corresponding to serum S4).

Example 11

Complete Inhibition of HIV Infection by the Rabbit Serum S4 at 1/50th Dilution

The capacity of the rabbit serum S4 from Aldernay to inhibit HIV infection was investigated at different dilutions. MT4 cells were incubated with HIV-1 LAI for 90 min at 37° C. in the presence of the pre-immune serum S0 at dilutions 1/25 and 1/50 and the immune serum S4 at dilutions 1/25, 1/50, 1/75 and 1/100. Cells were then centrifuged to remove the supernatant containing unbound HIV. Infected cells were suspended in fresh culture medium supplemented with the different rabbit sera. Cells were passaged on day 3 by the addition of 1 volume of fresh culture medium supplemented with the different sera. At 6 days post-infection, culture supernatants and cell extracts were assayed by ELISA for the concentration p24 (FIG. 13).

Clearly, there is a dose-dependent inhibition of HIV infection, reaching more than 99% inhibition at 1/50th dilution of S4. The degree of inhibition of S4 at dilutions 1/75 and 1/100 was 88 and 60%, respectively. The 50% inhibitory dilution of serum S4 against HIV-1 LAI infection of MT4 cells was estimated to be 1/110 (FIG. 13), whereas that of serum S5 was found to be 1/40 (FIG. 10).

Example 12

The Enhanced Accumulation of gp41 in the Triton Resistant Pellet Obtained from HIV-Infected Cells Cultured in the Presence of Anti-CBD-1 Antibodies At 6 days post-infection of the different samples presented in FIG. 13, Triton X-1 00®. soluble extracts were analyzed by immunoblotting for the presence of Gag proteins (FIG. 14, A and B), whereas Triton-resistant extracts were analyzed by immunoblotting for gp41 after solubilization in SDS (FIG. 14C).

In accord with complete inhibition of virus infection in cultures treated the anti-CBD-1 antibodies at dilutions 1/25 and 1/50 (FIG. 13), no Gag products were detectable (FIG. 14, A and B). It should be noted that when the level of Gag proteins in cultures treated with the anti-CBD-1 antibodies at dilutions 1/75 and 1/100 was still very much reduced compared with the corresponding controls, there was a marked increase in the level of Triton-resistant gp41 (FIG. 14C). The quantification of cell-associated p17 and gp41 bands observed in the infected-cells in the presence of 1/100 dilution of anti-CBD-1 serum indicated that the level of gp41 was increased by 6 fold although p17 was reduced by at least 6 fold. Therefore, at high dilutions when the inhibitory effect of the anti-CBD-1 antibodies was lower, there was a dramatic increase of gp41 associated in a Triton-resistant complex.

These observations point out that the anti-CBD-1 antibodies by interacting with the mature transmembrane envelope glycoprotein expressed on the cell surface cause aggregation of gp41 in the plasma membrane and its accumulation in a Triton-resistant complex.

The increased level of gp41 in cells treated with the immune serum should reflect the accumulation of gp41 in cells due to a reduced incorporation of gp41 in the newly released virus particles since no effect is observed on the Gag precursor and its mature products (FIG. 14). These results suggest the production of defective virus particles by HIV-infected cells cultured in the presence of anti-CBD-1 antibodies. Indeed, virus produced from HIV-infected cells cultured in the presence of S4 serum at 1/100th dilution manifested lower infectivity. The proportion of defective virus particles in this latter case was estimated to be around 40 to 45%.

Example 13

Association of Caveolin with Virus Particles

Caveolin 1 is expressed in MT4 cells as a 21 kDa protein. However, most of cellular caveolin remains insoluble in nonionic detergents but it is solubilized in an ionic detergent such as SDS. In order to investigate the fate of caveolin during HIV infection, cell extracts of HIV-infected cells were first prepared by lysis buffer containing 1% Triton X-100® and then the Triton-resistant pellet was suspended in PAGE sample buffer containing 1% SDS. Similarly, HIV recovered from the culture supernatant of HIV-infected cells was extracted with the lysis buffer containing Triton and then buffer containing SDS. Triton and SDS soluble fractions (lanes Trit. and lanes SDS) from the infected cells (panel Cell) and from the HIV pellet (panel HIV) were analyzed by immunoblotting using rabbit anti-p24 antibody and rabbit anti-caveolin 1 antibodies (FIG. 15).

In the infected cell, the Gag precursor p55 and its cleaved products p40 and p24 were recovered as Triton-soluble and Triton-resistant material, whereas in HIV particles, p24 was mostly recovered as Triton-soluble material (FIG. 15; the position of the Gag precursor p55, its partial cleavage product p40, and the mature viral core protein p24 is indicated on the right side). As it was expected, the majority of caveolin was recovered in the Triton-resistant fraction extracted from cells. On the other hand in HIV extracts, the anti-caveolin antibody reacted very strongly with a Triton-soluble protein of about 60 kDa that might correspond to an oligomeric form of caveolin (FIG. 15, the lower part of the figure). This is most likely the case, since caveolin in some cells is detectable as a 60 kDa protein.

The transformation of caveolin from a monomeric to an oligomeric form in the HIV particle might be the consequence of a specific event associated with the release of HIV particles from infected cells. Indeed, the 60 kDa-caveolin was only slightly detectable in the Triton-soluble fraction from infected cells, whereas no monomeric caveolin was found in HIV particles. Furthermore, in contrast with the monomeric caveolin, the 60-kDa caveolin is mostly soluble in Triton (FIG. 15; panel HIV, lane Trit.).

Partial oligomerization of caveolin is most probably a reflection of the cholesterol content at the plasma membrane of a given cell type. Indeed, the binding of caveolin to cholesterol has been reported to stabilize the formation of caveolin homo-oligomeric complexes (10). Consequently, the transformation of monomeric to oligomeric caveoliri could occur during HIV budding as a consequence of variation in the cholesterol content between HIV envelope and the host plasma membrane. In accord with this, the cholesterol-to-phospholipid molar ratio of the HIV envelope has been reported to be approximately 2.5 times of the host cell surface membrane (54). Furthermore, the lipid composition of the membrane of HIV displays unusually high content of cholesterol and sphingomyelin (54), which is a favorable environment for caveolin (10).

Example 14

The C-20 Peptide Corresponding to the Caveolin-Scaffolding Domain in Caveolin is Antigenic in Rabbits The scaffolding domain of caveolin (40,41), referred to as the C-20 peptide, has the following amino acid sequence:

DGIWKASFTTFTVTKYWFYR.    (SEQ ID No. 10)

A biotinylated C-20 peptide was synthesized as in Example 2. After synthesis the biotinylated C-20 peptide was solubilized in water containing 10% DMSO at a concentration of 2 mg/ml. 100 µg of this solution (corresponding to 50 µl) was mixed with 50 µg of streptavidin in 250 µl distilled water. This solution was then mixed with 250 µl of adjuvant; complete Freund's adjuvant (CFA) for the first injection and incomplete Freund's adjuvant (IFA) for the following injections. Rabbits (Fauves de Bourgogne) were injected intramuscularly with 500 µl of the antigen/adjuvant mixture. 10 ml of blood was collected from the rabbits before the first injection of antigen. This serum is referred to as S0 or pre-immune serum. The injection and bleeding dates of one rabbit, "Hermione," are shown in Table 2 below:

TABLE 2

| | |
|---|---|
| | Bleeding S0: day 0 |
| Injection 1: day 35 | |
| Injection 2: day 49 | Bleeding S1: day 63 |
| Injection 3: day 70 | Bleeding S2: day 77 |
| Injection 4: day 84 | Bleeding S3: day 91 |
| Injection 5: day 106 | Bleeding S4: day 112 |
| Injection 6: day 126 | Bleeding S5: day 133 |
| | Bleeding S6: day 153 |

All sera were tested by ELISA using 2 types of plates (PVC and Maxisorp) coated with the C-20 peptide. The results are presented in FIG. 16. After the first 2 injections, there was already a significant amount of antibodies against C-20 as observed at a dilution of 1/2000.

Example 15

The C-20 Peptide Elicits a Protective Immune Response Against HIV Infection in the MT4 Lymphocyte Cell Line The anti-HIV action of antibodies was tested by using HIV-1 LAI isolate on MT4 cells. Cells were infected with HIV by incubation at 37° C. for 90 min. The cell suspension was then centrifuged to remove the medium containing unbound HIV. The cell pellet was then suspended in fresh culture medium in the absence or presence of the anti-C-20 sera from Hermione at a dilution of 1/25. Cells were passaged every 2-3 days. The culture supernatant was assayed for the production of HIV by the p24 ELISA assay (FIG. 17).

These results show that antibodies against the C-20 peptide in caveolin are capable of inhibiting HIV infection. The pre-immune S0 and S1 sera had no apparent anti-HIV action whereas S2 and S3 (i.e., after the third and fourth immunization) had a very strong inhibitory activity; 77% and 98% respectively (FIG. 17).

Further immunization of rabbits with the C-20 peptide (following the fifth immunization) the neutralizing antibody declined drastically as the S4 and S5 sera had no significant effect on HIV infection. The reason for this latter effect remains to be elucidated. Whatever is the case, these observations provide further evidence for the implication of the caveolin-binding domain in the viral transmembrane glycoprotein during the HIV infectious cycle. Consequently, anti-C-20 antibodies could also be used as a means to block HIV infection.

The IC50 value of the rabbit Hermione S3 serum against HIV-1 LAI infection in MT4 cells is obtained around the 1/60th dilution.

Example 16

Inhibition of HIV Infection by the Anti-CBD-1 Antibodies Against Laboratory Adapted and Primary Viral Isolates in Primary CD4+ T Lymphocytes CD4+ lymphocytes were prepared from PBMC after depletion of CD8+ cells using Dynabeads M-450 CD8. CD4+ cells were then stimulated with PHA and cultured for 3 days in RPMI-1640 medium containing 10% fetal calf serum. Cell were then suspended in fresh culture medium containing IL-2. After 24 hours, cells were infected with the different isolates of HIV-1. Virus infection was monitored by measuring p24 ELISA in the culture supernatant at different days post infection.

The inhibitory action of the immune serum Aldernay S4 against the CBD-1 peptide was investigated in CD4+ primary T lymphocyte cultures infected with the T-lymphocyte tropic (X4) HIV-1 LAI, macrophage-tropic (R5) HIV-Ba-L, X4 HIV-1 ELI isolate from Zaire, an isolate resistant to the non-nucleoside RT inhibitor nevirapine (HIV-1 N199), an isolate resistant to the HIV protease inhibitor saquinavir (HIV-1 SR), and the primary isolate HIV-1 92UG037. Primary CD4+ T lymphocytes were incubated with different virus isolates for 90 min at 37° C. in the presence of the pre-immune serum Aldernay S0 (at 1/25, 1/50, and 1/100 dilution) and the immune serum Aldernay S4 (at 1/25, 1/50, and 1/100 dilution). Cells were then centrifuged to remove the supernatant containing unbound HIV. Infected cells were suspended in fresh culture medium supplemented with the different rabbit sera. Cells were passaged on day 3 by the addition of 1 volume of fresh culture medium supplemented with the different sera.

The preimmune serum S0 had no inhibitory effect on infection by HIV-1 Ba-L, HIV-1 SR, and HIV-1 92UGO37, while there was 25 and 50% enhancement of virus production in the case of HIV-1 LAI and HIV-1 199/HIV-1 ELI, respectively. A typical result of the S0 serum on HIV-1 LAI infection is shown in FIG. 18A. On the other hand, the immune serum S4 had a dose dependent inhibition of virus production, with IC95% values at 1/25-1/50 dilutions, and 1050 values at 1/50 1/100 dilutions (FIGS. 18A and B, and Table 3).

FIG. 19 shows the kinetics of inhibition of HIV infection by the anti-CBD-1 antibodies against R5 HIV-1 Ba-L and the HIV-1 isolate resistant to the HIV proease inhibitor saquinavir (HIV-1 SR) in primary CD4+ T lymphocyte culture.

Virus infection of CD4+ primary T lymphocytes was carried out as in the legend of FIG. 8 with HIV-1 Ba-L and HIV-1 SR in the absence (Control) or presence of the immune serum S4 at 1/125, 1/50, and 1/100 dilutions (as it is indicated in FIG. 19). Culture supernatants at 3, 4, and 5 days post-infection were assayed by ELISA for the concentration p24. Each point represents the mean of duplicate samples.

These observations indicate the potent anti-HIV action of the anti-CBD-1 antibodies in a primary cell culture permissive to HIV infection. Furthermore, the fact that anti-CBD-1 antibodies inhibit virus isolates that have specific modifications in their respective CBD-1 domain (See amino acid sequence of the CBD-1 peptide and sequences of HIV-1 LAI, Ba-L, ELI and 92UGO37) points out that the CBD-1 peptide is capable of eliciting broadly neutralizing antibodies.

TABLE 3

The inhibitory action of the immune serum against CBD-1 in primary CD4+ T lymphocytes against different laboratory and primary HIV-1 isolates.

| HIV-1 isolate | IC95 | IC50 |
| --- | --- | --- |
| LAI | 1/25th dilution | 1/40th dilution |
| Ba-L | 1/25th dilution | 1/50th dilution |
| HIV-1 ELI | 1/25th dilution | 1/50th dilution |
| HIV-1 N199 | 1/25th dilution | 1/50th dilution |
| HIV-1 RS | 1/50th dilution | >1/100th dilution |
| 92UGO37 | 1/25th dilution | 1/40th dilution |

The inhibitory action of the immune serum Aldernay S4 against the CBD-1 peptide was investigated in CD4+ primary T lymphocyte cultures infected with the T-lymphocyte tropic (X4) HIV-1 LAI, macrophage-tropic (R5) HIV-Ba-L, X4 HIV-1 ELI isolate from Zaire, an isolate resistant to the non-nucleoside RT inhibitor nevirapine (HIV-1 N1 99), an isolate resistant the HIV protease inhibitor saquinavir (HIV-I SR), and the primary isolate HIV-1 92UGO37.

Example 17

Enhanced Levels of Natural Antibodies Against the CBD-1 Epitope in HIV Positive Individuals The CBD-1 peptide was used in an ELISA assay to investigate the presence of natural antibodies against the CBD-1 epitope in HIV positive individuals. An OD value less than 0.2 is considered as negative.

Sera from healthy individuals did not react with the CBD-1 peptide. However, sera from HIV infected individuals reacted with the CBD-1 peptide, thus indicating the presence of natural antibodies against the CBD-1 epitope in HIV infected individuals.

Enhanced levels of natural antibodies against the CBD-1 epitope in HIV positive individuals considered as non-progressors (NP) were demonstrated as compared to the counterpart progressors (PR). These natural antibodies were of IgG type; no IgM were detectable. The results of this ELISA are set forth in Table 4 below using 2 µM of nonbiotinylated CBD-1.

TABLE 4

| NP Serums at 1/500 dilutions | IgG OD 450 nm | IgM OD 450 nm | IgT OD 450 nm |
| --- | --- | --- | --- |
| NP 49 | 0.084 | 0.005 | 0.059 |
| NP 53 | 0.115 | 0.002 | 0.058 |
| NP 63 | 0.531 | 0.003 | 0.267 |
| NP 84 | 0.218 | 0.034 | 0.145 |
| NP 98 | 0.308 | 0.005 | 0.153 |
| NP 114 | 0.188 | 0.01 | 0.095 |
| NP 152 | 0.257 | 0.015 | 0.143 |
| NP 549 | 0.167 | 0.004 | 0.105 |

| | IgG | IgM | IgT |
| --- | --- | --- | --- |
| PR | | | |
| PR 286 | 0.07 | 0.004 | 0.06 |
| PR 380 | 0.127 | 0.002 | 0.09 |
| PR 476 | 0.169 | 0.004 | 0.113 |
| PR 761 | 0.192 | 0 | 0.159 |
| PR 893 | 0.212 | 0.005 | 0.115 |
| Controls | | | |
| 2 | 0.019 | 0.003 | 0.01 |
| 3 | 0.004 | 0.003 | 0.003 |

TABLE 4-continued

| | | | |
|---|---|---|---|
| 4 | 0.005 | 0.006 | 0.008 |
| 5 | 0.029 | 0.003 | 0.017 |
| 6 | 0.016 | 0.009 | 0.013 |

The results of an ELISA in HIV positive individuals considered as non-progressors (NP) compared to progressors (PR) using the C-20 peptide are set forth in Table 5 below using 1 µM of the C-20 peptide. These results demonstrated that there is no apparent difference in the level of anti-C-20 antibodies between HIV positive individuals that are considered as non-progressors (NP) compared to progressors (PR). An OD value less than 0.2 is considered as negative.

TABLE 5

| NP Serums diluted 1/500 | IgG OD 450 nm | IgM OD 450 nm | IgT OD 450 nm |
|---|---|---|---|
| NP 49 | 0.252 | 0.023 | 0.255 |
| NP 53 | 0.319 | 0.002 | 0.211 |
| NP 63 | 0.494 | 0.009 | 0.305 |
| NP 84 | 0.49 | 0.024 | 0.308 |
| NP 98 | 0.43 | 0.007 | 0.25 |
| NP 114 | 0.474 | 0 | 0.284 |
| NP 152 | 0.274 | 0 | 0.173 |
| NP 549 | 0.435 | 0.041 | 0.253 |

| | IgG | IgM | IgT |
|---|---|---|---|
| PR | | | |
| PR 286 | 0.398 | 0.002 | 0.249 |
| PR 380 | 0.404 | 0.017 | 0.259 |
| PR 476 | 0.481 | 0 | 0.371 |
| PR 761 | 0.206 | 0.006 | 0.164 |
| PR 893 | 0.3 | 0.003 | 0.24 |
| Controls | | | |
| 2 | 0.124 | 0 | 0.083 |
| 3 | 0.086 | 0 | 0.051 |
| 4 | 0.154 | 0 | 0.102 |
| 5 | 0.197 | 0 | 0.169 |
| 6 | 0.153 | 0.012 | 0.169 |

Example 18

The CBD-1 Peptide, CBD-2 Peptide, CBM-1/TH-1 Peptide, CBM-1/TH-2 Peptide, CBM-2/TH-1 Peptide, CBM-2/TH-2 Peptide and the C-20 Peptide, as Well as SEQ ID No. 1 Elicit a Neutralizing Antibody Response and are Able to Provide Protection Against SIV in Monkeys Pigtailed macaques (*Macaca nemestrina*) were divided into fifteen groups of 5; a control group (Control), and 14 other groups, each group of five macaques receiving one of the immunogenic antigens of SEQ ID Nos. 1 to 18. The macaques are immunized intradermally twice at weeks 0 and 1 with 300 µg of the synthetic peptides. The control group is administered saline in the same amount.

The monkeys are boosted intramuscularly at weeks 2, 4 and 6 with a total of 300 µg of the synthetic peptides in 0.5 ml of QS-21 adjuvant. Antibody production against each of SEQ ID Nos. 1 to 18 is monitored at 3, 5, 7, and 10 weeks. The macaques are then challenged at 10 weeks (i.e., 3 weeks after the last immunization) intravenously with 100 50% tissue culture infected doses ($TCID_{50}$) of simian/human immunodeficiency virus strain DH12 ($SHIV_{DH12}MD14YE$).

Virus infection in these monkeys is followed by measuring the p24 concentration by ELISA in the serum at 15, 30, 45, 60 and 90 days post-infection. ELISA against p24, neutralization assays in MT-4 cells and virus load measurements are performed at days 15, 30, 45, 60 and 90 post-infection. Results from these tests show a significant reduction of in vivo virus infection. Neutralization antibody titers increased over time in the immunized animals. The different techniques for monitoring SIV infection in monkeys was as described before (55, 56, 57).

Example 19

Making of Polyclonal and Monoclonal Antibodies

Each of SEQ ID Nos. 1 to 18 are injected into different mice and polyclonal and monoclonal antibodies are made following the procedure set forth in Sambrook et al supra.

More specifically, mice are immunized with the immunogenic antigens comprising the above mentioned SEQ ID Nos. 1 to 18 conjugated to keyhole limpet hemocyanin using glutaraldehyde or EDC as is well known in the art. The complexes can also be stabilized by crosslinking as described in WO 00/37483. The immunogen is then mixed with an adjuvant. Each mouse receives four injections of 10 μg to 100 μg of immunogen, and after the fourth injection, blood samples are taken from the mice to determine if the serum contains antibodies to the immunogen. Serum titer is determined by ELISA or RIA. Mice with sera indicating the presence of antibody to the immunogen are selected for hybridoma preparation. Immunization of mice and preparation of antibody producing hybridoma cell lines are as described before (58, 59, 60).

Spleens are removed from immune mice and single-cell suspension is prepared. Cell fusions are performed essentially as described by Kohler et al. (58). Briefly, P365.3 myeloma cells (ATTC Rockville, Md.) or NS-1 myeloma cells are fused with spleen cells using polyethylene glycol as described (58, 59, 60). Cells are plated at a density of $2\times10^5$ cells/well in 96-well tissue culture plates. Individual wells are examined for growth and the supernatants of wells with growth are tested for the presence of specific antibodies by ELISA or RIA using the specific immunogenic antigens of SEQ ID Nos. 1 to 18 a target protein. Cells in positive wells are expanded and subcloned to establish and confirm monoclonality.

Clones with the desired specificities are expanded and grown as ascites in mice or in a hollow fiber system to produce sufficient quantities of antibodies for characterization and assay development. Antibodies are tested for binding to each immunogenic antigen of SEQ ID Nos. 1 to 18 to determine which are specific for these antigens.

Monoclonal antibodies against each one of SEQ ID Nos. 1 to 18 are prepared in a similar manner by mixing specified immunogenic antigens together, immunizing an animal, fusing spleen cells with myeloma cells and isolating clones which produce antibodies specific for the Immunogenic antigens.

Example 20

Enhanced Levels of Natural Antibodies Against the Epitopes of SEQ ID No. 1, CBD-2, CBM-1/TH-1, CBM-1/TH-2, CBM-2/TH-1 and CBM-2/TH-2, as Well as Their Variants in HIV Positive Individuals SEQ ID Nos. 1 to 18 are used in an ELISA assay to investigate the presence of natural antibodies against these epitopes in HIV positive individuals.

Sera from healthy individuals do not react with SEQ ID Nos. 1 to 18. However, sera from HIV infected individuals react with SEQ ID Nos. 1 to 18, thus indicating the presence of natural antibodies against these epitopes in HIV infected individuals.

Enhanced levels of natural antibodies against the epitopes of SEQ ID No. 1 to 9 and 11 to 18 in HIV positive individuals considered as non-progressors (NP) are demonstrated as compared to the counter-part progressors (PR).

This example demonstrates that the immunogenic antigens of the present invention can be used for diagnostic purposes.

While the invention has been described in terms of the various preferred embodiments, the skilled artisan will appreciate that various modifications, substitutions, omissions and changes may be made without departing from the scope thereof. Accordingly, it is intended that the present invention be limited by the scope of the following claims, including equivalents thereof.

Example 21

Generation of Human Monoclonal Antibodies

SEQ ID Nos. 1 to 9 and 11 to 18 are used in an ELISA assay to investigate the presence of antibodies against these epitopes in HIV positive individuals: Five individuals are selected because of elevated titers of neutralizing antibodies against the peptides with SEQ ID Nos. 1 to 9 and 11 to 18. These individuals are referred to as high producers of neutralizing antibodies, HPNA.

Generation of human monoclonal antibodies producing cell lines are performed as described previously (44, 61, 62). Briefly, after Ficoll isolation, peripheral blood B-lymphocytes are transformed by the Eppstein-Barr virus and cultured at concentration ranging from 50,000 to 100,000 cells per well. After 2-4 weeks, the supernatants from such cultures are assayed for antibodies against the peptides SEQ ID Nos. 1 to 18, using ELISA methodology. These cells are shown to produce antibodies against the gp41-related peptides SEQ ID Nos. 1 to 9 and 11 to 18 but not against peptide C-20 SEQ ID No. 10, thus showing their specificity. To stabilize antibody production, the lymphoblastoid cell lines are fused with heteromyelomas to generate hybridomas and subsequently cloned.

Several human monoclonal antibodies are generated by this technique. These monoclonal antibodies that react specifically with the peptides SEQ ID Nos. 1 to 9 and 11 to 18, have the capacity to block infection of primary CD4$^+$ T lymphocytes by different types and subtypes of HIV. These monoclonal antibodies are purified by conventional techniques using protein NG-agarose and are used to treat HIV-infected individuals by intravenous injection of 10-50 mg antibody preparation. Fifteen days after injection of antibodies, there is 40 to 50% reduction of virus titers as measured by Polymerase Chain Reaction (PCR) amplification using extracts from $10 \times 10^6$ PBMC.

Example 22

Isolation of New Anti-HIV Molecules that Inhibit Interaction of Peptides SEQ ID Nos. 1 to 9 and 11 to 18 with Caveolin The affinity of biotin to bind avidin is very high. Consequently, peptides that are biotinylated bind strongly to the solid matrix avidin-agarose. By this procedure it is then possible to purify proteins, peptides or various other molecules which interact with the biotinylated peptides. For an example, the biotinylated CBD-1 peptide bound to avidin-agarose is used in FIG. 6 for the purification of caveolin.

Biotinylated peptides SEQ ID Nos. 1 to 9 and 11 to 18 were synthesized by coupling the biotin residue at the $NH_2$-terminal end of these peptides. These peptides bound to avidine-agarose generate caveolin-binding matrices as described in FIG. 6 or generate matrices that have the capacity to purify anti-HIV molecules that bind peptides SEQ ID Nos. 1 to 9 and 11 to 18.

In respect to the caveolin-binding matrices, following incubation of such matrices with cellular extracts, caveolin becomes specifically bound to the peptides SEQ ID Nos. 1 to 9 and 11 to 18, under similar experimental conditions as stated for the Example 5. However, if this latter reaction is carried out in the presence if interfering molecules referred to as CBD-CAV 1, CBD-CAV 2, CBD-CAV 3 then caveolin can no longer bind to the peptides SEQ ID Nos. 1 to 9 and 11 to 18, because of interference by molecules such as CBD-CAV 1, CBD-CAV 2, CBD-CAV 3. This latter experimental procedure could also be carried out by replacing the caveolin preparation by the peptide C-20 of SEQ ID No. 10. This technique which uses either caveolin or peptide C-20 provides an efficient method for the isolation of anti-HIV molecules that either interact with the peptides SEQ ID Nos. 1 to 9 and 11 to 18, or interact with caveolin/C-20. Two types of anti-HIV molecules therefore are selected: 1) those interacting with caveolin; 2) those interacting with the transmembrane envelope glycoprotein of HIV. This characterization of the isolated inhibitory molecules is carried out by using matrices containing peptides SEQ ID Nos. 1 to 9 and 11 to 18 or matrices containing caveolin/C-20 SEQ ID No. 10. Both subtypes of these inhibitors prevent infection of permissive cells by various HIV isolates.

In respect to matrices that have the capacity to purify anti-HIV molecules that bind peptides SEQ ID Nos. 1 to 9 and 11 to 18, such matrices are incubated with different existing molecules at 20 to 37° C. for 45 minutes. The matrices are then washed extensively, and the molecules bound to the specific matrices are recovered by elution buffer. By this process, we were able to isolate anti-HIV molecules that by their capacity to interact with peptides SEQ ID Nos. 1 to 9 and 11 to 18, can interact with the transmembrane envelope glycoprotein of HIV.

REFERENCES

1. DONG, X. N., X. YI, M. P. DIERICH, and B. K. CHEN 2001. N- and C-Domains of HIV-1 gp41: mutation, structure and functions. Immunology Letters. 75:215-220.
2. CHAN, D. C., D. FASS, J. M. BERGER, and P. S. KIM 1997. Core structure of gp41 from the HIV envelope glycoprotein. Cell 89: 263-273.
3. WEISENHORN, W., A. DESSEN, S. C. HARRISON, J. J. SKEHEL, and D. C. WILEY 1997. Atomic structure of the ectodomain from HIV-1 gp41. Nature 387:346-348.
4. CHAN, D. C., and P. S. KIM 1998. HIV Entry and its inhibition. Cell 93:681-684.
5. KILBY, J. M., S. HOPKINS, T. M. VENETTA, B. D I MASSIMO, G. A. CLOUD, J. Y. LEE, L. ALLDREDGE, E. HUNTER, D. LAMBERT, D. BOLOGNESI, T. MATHEWS, M. R. JOHNSON, M. NOWAK, G. M. SHAW, and M. S. SAAG 1998; Potent suppression of HIV-1 replication in humans by T-20, a peptide inhibitor of gp41-mediated virus entry. Nature Medicine 4: 1302-1307.
6. NISOLE, S., B. KRUST, and A G. HOVANESSIAN 2002. Anchorage of HIV on permissive cells leads to co-aggregation of viral particles with surface nucleolin at membrane raft microdomains. Exp. Cell Res. 276:155-173.
7. BISHOP, N. E. 1997. An update on non-clathrin-coated endocytosis. Rev. Med. Virol. 7:199-209.
8. BROWN, D. A., and E. LONDON 2000. Structure and function of sphingolipid- and cholesterol-rich membrane rafts. J. BIOL. Chem. 275:17221-17224.
9. KURZCHALIA, T. V., and R. G. PARTON 1999. Membrane microdomains and caveolae. Curr. Opin. Cell Biol. 11:432-431.
10. SMART, E. J., G. A. GRAF, M. A. Mc NIVEN, W. C. SESSA, J. A. ENGELMAN, P. E. SCHERER, T. OKAMOTO, and M. P. LISANTI 1999. Caveolins, liquid-ordered domains and signal transduction. MOL. CELL. BIOL. 19:7289-7304.
11. HARDER, T., P. SCHEIFFELE, P. VERKADE, and K. SIMONS 1998. Lipid domain structure of the plasma membrane revealed by patching of membrane components. J. CELL. BIOL. 141:929-942.
12. CAMPBELL, S. M., S. M. CROWE, and J. MAK 2001. Lipid rafts and HIV-1: from viral entry to assembly of progeny virions. J CLIN. Virol. 22:217-227.
13. HUG, P., H. M. J. LIN, T. KORTE, X. XIAO, D. DIMITROV, J. M. WANG, PURI, and R. BLUMENTHAL 2000. Glycosphingolipids promote entry of a broad range of human immunodeficiency virus type 1 isolated into cell lines expressing CD4, CXCR4, and/or CCR5. J. Virol 74:6377-6385.
14. MANES, S., G. DEL REAL, R. A. LACALLE, P. LUCAS, C. GOMEZ-MOUTON, S SANCHEZ-PALOMINO, R. DELGADO, J. ALCAMI, E. MIRA, and C. MARTINEZ-A 2000. Membrane raft microdomains mediate lateral assemblies required for HIV-1 infection. EMBO reports. 1:190-196.
15. LIANO, M., T. KELLY, M. VANEGAS, M. PERETZ, T. E. PETERSON, R. D. SIMARI, and E. M. POESCHLA 2002. Blockade of human immunodeficiency virus type I expression by caveolin-1 J. VIROL. 76:9152-9164.
16. NGUYEN, D. H., and J. E. K. HILDRETH 2000. Evidence for budding of human immunodeficiency virus type 1 selectively from glycolipid enriched membrane lipid rafts. J. VIROL 74:3264-3272.
17. ONO, A., and E. O. FREED 2001. Plasma membrane rafts play a critical role in HIV-1 assembly and release PROC. NATL. ACAD. SCIEN USA 98: 13925-13930.
18. MOORE, J. P., B. A. JAMESON, R. A. WEISS, and Q. J. SATTENTAU 1993. The HIV-cell fusion reaction, .pp. 233-289. In J.E. BENTZ (ed.). Viral Fusion mechanisms. CRC Press, Boca Raton, F1.
19. BERGER, E. A. 1997. HIV entry and tropism: the chemokine receptor connection. AIDS. 1:S3-S16.
20. WYATT, R., and J. SODROSKI 1998. The HIV-1 envelope glycoproteins: fusogens, antigens, and immunogens. Science 280:1884-1888.
21. NISOLE, S., B. KRUST, C. CALLEBAUT, G. GUICHARD, S. MULLER, J P BRIAND and A. G. HOVANESSIAN 1999. The anti-HIV pseudopeptide HB-19 forms a complex with the cell-surface expressed nucleolin independent of heparin sulfate proteoglycans. J. BIOL Chem. 274:27875-27884.
22. NISOLE, S. E. A. SAID, C. MISCHE, M. C. PREVOST, B. KRUST, P. BOUVET, A. BIANCO, J. P. BRIAND, and A. G. HOVANESSIAN 2002. The anti-HIV pentameric pseudopeptide HB-19 binds the C-terminal end of nucleolin and prevents anchorage of virus particles in the plasma membrane of target cells. J. BIOL. CHEM. 277:20877-20886.
23. UGOLINI, S., I. MONDOR and Q. J. SATTENTAU 1999. HIV-1 attachment: another look. Trends Microbiol. 7:144-149.
24. VALENZUELA A., J. BLANCO, B. KRUST, R. FRANCO and A. G. HOVANESSIAN 1997. Neutralizing antibodies against the V3 loop of the HIV-1 gp 120 block the CD4-dependent and independent binding of virus to cells. J. VIROL 71:8289-8298.
25. DEL REAL, G., S. JIMENEZ-BARANDA, R. A. LACALLE, E. MIRA, P. LUCAS, C. GOMEZ-MOUTON, A. C. CARRERA, C. MARTINEZ-A, and S. MANES. 2002 Blocking of HIV-1 infection by targeting CD4 to nonraft membrane microdomains. J. Exp. Med. 196:293-301.
26. NGUYEN, D. H., and D. TAUB 2002. CXCR4 function requires membrane cholesterol: implications for HIV infection. J. IMMUNOL. 168:4121-4126.
27. LIANO, M., L. M. CIMAKASKY, R. HAMPTON, D. H. NGUYEN, and E. K. HILDRETH 2001. Lipid rafts and HIV pathogenesis: host membrane cholesterol is required for infection by HIV type I. AIDS Res. Hum. Retroviruses. 17:1009-1019.
28. ALFSEN, A., P. INIGUEZ, E. BOUGUYON, and M. BOMSEL 2001. Secretory IgA specific for a conserved epitope on gp41 envelope glycoprotein inhibits epithelial transcytosis of HIV-1. J. Immunol 166:6257-6265.
29. KILBY et al, 1998 Nature Medicine, volume 4, No. 11.
30. NEIMARK, J., and J. P. BRIAND 1993. Development of a fully automated multichannel peptide synthesizer with integrated TFA cleavage capability. Peptide Res. 6:219-228.
31. KING, D., C. FIELDS, and G. FIELDS 1990. A cleavage method which minimizes Side reactions following Fmoc solid-phase peptide synthesis Ins. J. Peptide Protein Res 36:255-266.
32. NISOLE, S., B. KRUST, E. DAM, A. BIANCO, N. SEDDIKI, S. LOAEC, C. CALLEBAUT, G. GUICHARD, S. MULLER, J. P. BRIAND, and A. G. HOVANESSIAN 2000. The HB-19 pseudopeptide 5 [K $\psi$ (CH$_2$N)PR]-TASP inhibits attachment of T-lymphocyte and macrophage-tropic HIV to permissive cells. AIDS Res. Hum. Retroviruses. 16:237-249.
33. CALLEBAUT, C., S. NISOLE, J. P. BRIAND, B. KRUST, and A. G. HOVANESSIAN 2001. Inhibition of HIV infection by the cytokine midkine. Virology 281:248-264.
34. SAID, E. A., B. KRUST, S. NISOLE, J. SVAB, J. P. BRIAND, and A. G. HOVANESSIAN 2002. The anti-HIV cytokine midkine binds the cell-surface-expressed nucleolin as a low affinity receptor. J. BIOL. CHEM. 277:37492-37502.
35. LAURENT-CRAWFORD, A. G., and A. G. HOVANESSIAN 1993. The cytopathic effect of human immunodeficiency virus is independent of high levels of unintegrated viral DNA accumulated in response to superinfection of cells. J. Gen. VIROL. 74:2619-2628.
36. BABOONIAN, C., A. DALGLEISH, L. BOUNTIFF, J. GROSS, S. OROSZLAN, G. RICKETT, C. SMITH-BURCHNELL, P. TROKE, and J. MERSON 1991. HIV-1 proteinase is required for synthesis of pro-viral DNA. Biochem. Biophys. Res. Commun. 179:1724.
37. DEEKS, S. G., M. SMITH, M. HOLODNIY, and J. O. KAHN 1997. HIV-1 protease inhibitors JAMA. 277:145-153.

38. TOMASSELLI, R., A. G., and R. L. HEINRIKSON 2000. Targeting the HIV-protease in AIDS therapy: a current clinical perspective Biochim. Biophys. Acta. 1477:189-214.
39. KUIKEN, C, B. FOLEY, B. HAHN, P. MARX, F. McCURCHAN, J. MELLORS, J. MULLINS, J. S. SODROSKI, and B. KORBER 2000. HIV Sequence Compendium 2000. Theoretical Biology and Biophysics Group T-10, Los Alamos National Laboratory, Los Alamos, N. Mex.
40. COUET, J., S. LI, T. OKAMOTO, T. IKEZU, and M. P. LISANTI 1997. Identification of peptide and protein ligands for the caveolin-scaffolding domain J. BIOL. Chem. 272:6525-6533.
41. OKAMOTO, T., A. SCHLEGEL, P. E. SCHERER, and M. P. LISANTI 1998. Caveolins, a family of scaffolding proteins for organizing "reassembled signaling complexes" at the plasma membrane. J. BIOL. Chem. 273:5419-5422.
42. Wagner, R., Y. Shao, and H. Wolf 1999. Correlates of protection, antigen delivery and molecular epidemiology: basis for designing an HIV vaccine. Vaccine. 17:13-14.
43. Sattentau, Q. J., M. Moulard, B. Brivet, F. Botto, J. C. Guillemot, I. Mondor, P. Poignard, and S. Ugolini 1999. Antibody neutralization of HIV-1 and the potential for vaccine design. Immunology letters. 66:143-149.
44. Viveros, M., C. Dickey, J. P. Cotropia, G. Gevorkian, C. Larralde, K. Broliden, M. Levi, A. Burgess, C. Cao, D. B. Weiner, M. G. Agadjanian, and K. E. Ugen 2000. Characterization of a novel human immunodeficiency virus type I neutralizable epitope within the immunodominant Region of gp41. Virology. 270:135-145.
45. Muster, T., R. Guinea, M. Trkola, M. Purtscher, A. Klima, F. Steindl, P. Palese, and H. Katinger 1994. Cross-neutralizing activity against divergent human immunodeficiency virus type 1 isolates induced by the gp41 sequence ELDKWAS. J. Virol. 68:4031-4034.
46. Moore, J. P., P. W. H. I. Parren, and D. R. Burton 2001. Genetic subtypes, humoral immunity, and human immunodeficeincy virus type 1 vaccine development. J. Virol. 75:5721-5729.
47. Parker, C. E., L. J. Deterding, C. Hager-Braun, J. M. Binley, N. Schûlke, H. Katinger, J. P. Moore, and K. B. Tomer 2001. Fine definition of the epitope on the gp41 glycoprotein of human immunodeficiency virus type I for the neutralizing monoclonal antibody 2F5. J. Virol. 75:10906-10911
48. Golding, H., M. Zaitseva, E. de Rosny, L. R. King, J. Manischewitz, I. Sidorov, M. K. Gorny, S. Zolla-Pazner, D. S. Dimitrov, and C. D. Weiss 2002. Dissection of human immunodeficiency virus type 1 entry with neutralizing antibodies to gp41 fusion intermediates. J. Virol. 76:6780-6790.
49. Igarashi, T., C. Brown, A. Azadegan, N. Haigwood, D. Dimitrov, M. A. Martin, and R. Shibata 1999. Human immunodeficiency type I neutralizing antibody accelerates clearance of cell-free virions from blood plasma. Nat. Med. 5:211-216.
50 Shibata, R., T. Igarashi, N. Haigwood, A. Buckler-White, R. Ogert, W. Ross, R. Willey, M. W. Cho, and M. A. Martin 1999. Neutralizing antibody directed against the HIV-1 envelope glycoprotein can completely block HIV-1/SIV chimeric virus infections of macaque monkeys. Nat. Med. 5:204-210.
51. Kahn, P. 2003. Cent Gardes vaccine meeting highlights role of antibodies in protection. IAVI Report. 6:1-2.
52. Wei, X., J. M. Decker, H. Liu, Z. Zhang, R. B. Arani, J. M. Kilby, M. S. Saag, X. Wu, G. M. Shaw, and J. C. Kappes 2002. Emergence of resistant human immunodeficiency virus type 1 in patients receiving fusion inhibitor (T-20) monotherapy. Antimicrobial Agents and Chemotherapy. 46:1896-1905.
53. Korber, B. T. M., C. Brander, B. F. Haynes, R. Koup, C. Keiken, J. P. Moore, B. D. Walker, and D. I. Watkins 2002. HIV Molecular Immunology. Los Alamos Natl. Lab. Theor. Biol. Biophys., Los Alamos, N. Mex.: http://hiv-web.lanl.gov/immunology
54. Aloia, R. C., H. Tian, and F. C. Jensen 1993. Lipid composition and fluidity of the human immunodeficiency virus envelope and host cell plasma membranes. Proc. Natl. Acad. Sci. USA. 90:5181-5185.
55. Walther-Jallow, L., C. Nilsson, J. Sôderlund, P. Ten Haaft, B. Mâkitalo, P. Biberfeld, P. Bôttiger, J. Heeney, G. Biberfeld, and R. Thorstensson 2001. Cross-protection against mucosal simian immunodeficienncy virus (SIVsm) challenge in human immunodeficiency virus type 2-vaccinated cynomolgus monkeys. J. gen. Virol. 82:1601-1612.
56. Letvin, N. L., S. Robinson, D. Rohne, M. K. Axthelm, J. W. Fanton, M. Bilska, T. J. Palker, H. X. Liao, B. F. Haynes, and D. C. Montefiori 2001. Vaccine elicited V3 loop-specific antibodies in rhesus monkeys and control of a simian-human immunodeficiency virus expressing a primary patient human immunodeficiency virus type 1 isolate envelope. J. Virol. 75:4165-4175.
57. Cafaro, A., F. Titti, C. Fracasso, T. M. Maggiorella, S. Baroncelli, A. Caputo, D. Goletti, A. Borsetti, M. Pace, E. Fanales-Belasio, B. Ridolfi, D. R. M. Negri, L. Sernicola, R. Belli, F. Corrias, I. Macchia, P. Leone, Z. Michelini, P. T. Haaft, S. Butto, P. Verani, and B. Ensoli 2001. Vaccination with DNA containing tat coding sequences and unmethylated CpG motifs protects cynomolgus monkeys upon infection with simian/human immunodeficiency virus (SHIV89.6P). Vaccine. 19:2862-2877.
58. Kôhler, G., and C. Milstein 1975. Continuous cultures of fused cells secreting antibody of predefined specificity. Nature. 256:45-97.
59. Krust, B., A. G. Laurent, A. Le Guern, O. Jeannequin, L. Montagnier, and A. G. Hovanessian 1988. Characterization of a monoclonal antibody specific for the HIV-1 precursor glycoprotein. AIDS. 2:18-24.
60. Hovanessian, A. G., A. G. Laurent, J. Chebath, J. Galabru, N. Robert, and J. Svab 1987. Identification of 69 kd and 100 kd forms of 2-5A synthetase in interferon-treated human cells by specific monoclonal antibodies. EMBO J. 6:1273-1280.
61. Desgranges, C., V. Boyer, S. Souche, S. Sprecher, A. Burney, R. C. Gallo, J. Bernard, B. Reveil, and D. Zagury 1988. Monoclonal antibodies to HIV in a non-infected, immunized volunteer. Lancet. 8591:935-936.
62. Boyer, V., H. Broly, S. Souche, P. Madaule. J. Rossier, D. Zagury, and C. Desgranges 1991. Characterization and large production of human monoclonal antibodies against the HIV-1 envelope. Clin. Exp. immunol. 83:452-459.
63. Huls G A, Heijnen I A, Cuomo M E, Koningsberger J C, Wiegman L, Boel E, van der Vuurst de Vries A R, Loyson S A, Helfrich W, van Berge Henegouwen G P, van Meijer M, de Kruif J, Logtenberg T. 1999. A recombinant, fully human monoclonal antibody with antitumor activity constructed from phage-displayed antibody fragments. Nat Biotechnol 3:276-81.
64. Gauduin M C, Parren P W, Weir R, Barbas C F, Burton O R, Koup R A. 1997. Passive immunization with a human monoclonal antibody protects hu-PBL-SCID mice against challenge by primary isolates of HIV-1. Nat Med 12:1389-93.

What is claimed is:

1. A pharmaceutical composition comprising at least one peptide consisting of

W-N-N-M-T-W-M-E-W    (SEQ ID No. 8)

or a pharmaceutically acceptable salt of said at least one peptide, and a pharmaceutically acceptable vehicle.

2. The pharmaceutical composition according to claim 1, wherein said at least one peptide, other than SEQ ID NO: 8, is glycosylated, has introduced therein two cysteine residues to form a disulfide bridge, or is phosphorylated.

3. The pharmaceutical composition according to claim 1, wherein said at least one peptide, other than SEQ ID NO: 8, has fatty acids attached to the N- or C-terminals.

4. The pharmaceutical composition according to claim 1 further comprising an adjuvant.

5. The pharmaceutical composition according to claim 4, wherein said adjuvant is selected from the group of: Complete Freund's Adjuvant, Incomplete Freund's Adjuvant, motanide incomplete seppic adjuvant, the Ribi adjuvant system, Titer Max, muramyl peptides, Syntex Adjuvant Formulation, aluminum hydroxide, aluminum phosphate, aluminum salt adjuvants, Gerbu® adjuvants, nitrocellulose absorbed antigen, encapsulated or entrapped antigen, Quil A and QS-21, CpG oligonucleotides, and double stranded RNA molecules.

6. The pharmaceutical composition according to claim 1, which is encapsulated with a polymer, liposome, or micelle.

7. The pharmaceutical composition according to claim 1 or claim 4, wherein the at least one peptide, other than SEQ ID NO: 8, is associated covalently or non-covalently or is in a mixture with a foreign peptide or a foreign antigen.

8. A composition comprising at least one peptide consisting of W-N-N-M-T-W-M-E-W (SEQ ID NO. 8).

9. A kit to reduce to practice a method to measure the presence of neutralizing antibodies in a biological sample from a mammal, comprising at least one peptide according to claim 8, reagents necessary for the immunological reaction, and reagents necessary for the detection of the immunological complex.

10. A method to measure the presence of neutralizing antibodies in a biological sample from a mammal comprising contacting the biological sample with a peptide according to claim 8 under conditions that allow the formation of an immunological complex; and detecting the immunological complex that is formed.

* * * * *

UNITED STATES PATENT AND TRADEMARK OFFICE
CERTIFICATE OF CORRECTION

| | | |
|---|---|---|
| PATENT NO. | : 8,173,767 B2 | |
| APPLICATION NO. | : 12/073887 | |
| DATED | : May 8, 2012 | |
| INVENTOR(S) | : Ara Hovanessian et al. | |

It is certified that error appears in the above-identified patent and that said Letters Patent is hereby corrected as shown below:

Claim 8, col. 52, lines 19-20,
"8. A composition comprising at least one peptide consisting of
W-N-N-M-T-W-M-E-W (SEQ ID NO. 8)." should read
--8. A peptide consisting of W-N-N-M-T-W-M-E-W (SEQ ID NO: 9).--.

Signed and Sealed this
Twenty-fourth Day of July, 2012

David J. Kappos
*Director of the United States Patent and Trademark Office*

SEQUENCE LISTING

<160> NUMBER OF SEQ ID NOS: 21

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: caveolin
      binding motif in which Xaa is any amino acid
<220> FEATURE:
<221> NAME/KEY: VARIANT
<222> LOCATION: (2)..(5)
<223> OTHER INFORMATION: Xaa is any amino acid Ala, Gly, Val, Leu, Ile,
      Asn, Met, Cys, Ser, Thr, Gln, Asp, Glu, Lys, Arg, His, or Pro
<220> FEATURE:
<221> NAME/KEY: VARIANT
<222> LOCATION: (7)..(8)
<223> OTHER INFORMATION: Xaa is any amino acid Ala, Gly, Val, Leu, Ile,
      Asn, Met, Cys, Ser, Thr, Gln, Asp, Glu, Lys, Arg, His, or Pro

<400> SEQUENCE: 1

Trp Xaa Xaa Xaa Xaa Trp Xaa Xaa Trp
 1               5

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: caveolin
      binding domain corresponding to amino acids 619 to
      633 of HIV-1

<400> SEQUENCE: 2

Leu Glu Gln Ile Trp Asn Asn Met Thr Trp Met Gln Trp Asp Lys
 1               5                  10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: caveolin
      binding domain corresponding to amino acids 662 to
      676 of HIV-2

<400> SEQUENCE: 3

Leu Thr Pro Asp Trp Asn Asn Met Thr Trp Gln Glu Trp Glu Arg
 1               5                  10                  15

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: caveolin
      binding domain corresponding to amino acids 604 to
      633 of HIV-1

<400> SEQUENCE: 4

Cys Thr Thr Ala Val Pro Trp Asn Ala Ser Trp Ser Asn Lys Ser Leu
 1               5                  10                  15
Glu Gln Ile Trp Asn Asn Met Thr Trp Met Gln Trp Asp Lys
            20                  25                  30

<210> SEQ ID NO 5
<211> LENGTH: 26
<212> TYPE: PRT

```
<213> ORGANISM: Artificial Sequence
<220> FEATURE:
<223> OTHER INFORMATION: Description of Artificial Sequence: caveolin
      binding domain corresponding to amino acids 651 to
      676 of HIV-1

<400> SEQUENCE: 5

Cys His Thr Thr Val Pro Trp Pro Asn Asp Ser Leu Thr Pro Asp Trp
 1               5                  10                  15

Asn Asn Met Thr Trp Met Gln Trp Asp Lys
            20                  25

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: caveolin
      binding domain corresponding to amino acids 651 to
      676 of HIV-2

<400> SEQUENCE: 6

Cys His Thr Thr Val Pro Trp Pro Asn Asp Ser Leu Thr Pro Asp Trp
 1               5                  10                  15

Asn Asn Met Thr Trp Gln Glu Trp Glu Arg
            20                  25

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: caveolin
      binding domain corresponding to amino acids 604 to
      676 of HIV-1

<400> SEQUENCE: 7

Cys Thr Thr Ala Val Pro Trp Asn Ala Ser Trp Ser Asn Lys Ser Leu
 1               5                  10                  15

Glu Gln Ile Trp Asn Asn Met Thr Trp Gln Glu Trp Glu Arg
            20                  25                  30

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Caveolin
      binding motif

<400> SEQUENCE: 8

Trp Asn Asn Met Thr Trp Met Glu Trp
 1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Caveolin
      binding motif

<400> SEQUENCE: 9

Trp Asn Asn Met Thr Trp Gln Glu Trp
 1               5

<210> SEQ ID NO 10
```

```
<211> LENGTH: 20
<212> TYPE: PRT
<213> ORGANISM: Artificial Sequence
<220> FEATURE:
<223> OTHER INFORMATION: Description of Artificial Sequence: C-20
      peptide scaffolding domain of caveolin from amino acids 82
      to 101 of caveolin-1

<400> SEQUENCE: 10

Asp Gly Ile Trp Lys Ala Ser Phe Thr Thr Phe Thr Val Thr Lys Tyr
 1               5                  10                  15

Trp Phe Tyr Arg
            20

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Variant of
      SEQ ID No. 2 in which Xaa is any amino acid that can be added at
      the N-terminal or C-terminal of the sequence. The maximum number
      of these added amino acids (Xaa) can be 40.
<220> FEATURE:
<221> NAME/KEY: VARIANT
<222> LOCATION: (1)
<223> OTHER INFORMATION: Xaa is any amino acid Ala, Gly, Val, Leu, Ile,
      Asn, Phe, Trp, Tyr, Met, Cys, Ser, Thr, Gln, Asp, Glu, Lys, Arg,
      His, or Pro
<220> FEATURE:
<221> NAME/KEY: VARIANT
<222> LOCATION: (17)
<223> OTHER INFORMATION: Xaa is any amino acid Ala, Gly, Val, Leu, Ile,
      Asn, Phe, Trp, Tyr, Met, Cys, Ser, Thr, Gln, Asp, Glu, Lys, Arg,
      His, or Pro

<400> SEQUENCE: 11

Xaa Leu Glu Gln Ile Trp Asn Asn Met Thr Trp Met Gln Trp Asp Lys
 1               5                  10                  15

Xaa

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Variant of
      SEQ ID No. 3 in which Xaa is any amino acid, that can be added at
      the N-terminal or C-terminal of the sequence. The maximum number
      of these added amino acids (Xaa) can be 40.
<220> FEATURE:
<221> NAME/KEY: VARIANT
<222> LOCATION: (1)
<223> OTHER INFORMATION: Xaa is any amino acid Ala, Gly, Val, Leu, Ile,
      Asn, Phe, Trp, Tyr, Met, Cys, Ser, Thr, Gln, Asp, Glu, Lys, Arg,
      His, or Pro
<220> FEATURE:
<221> NAME/KEY: VARIANT
<222> LOCATION: (17)
<223> OTHER INFORMATION: Xaa is any amino acid Ala, Gly, Val, Leu, Ile,
      Asn, Phe, Trp, Tyr, Met, Cys, Ser, Thr, Gln, Asp, Glu, Lys, Arg,
      His, or Pro

<400> SEQUENCE: 12

Xaa Leu Thr Pro Asp Trp Asn Asn Met Thr Trp Gln Glu Trp Glu Arg
 1               5                  10                  15

Xaa

<210> SEQ ID NO 13
<211> LENGTH: 15
<212> TYPE: PRT
```

```
<213> ORGANISM: Artificial Sequence
<220> FEATURE:
<223> OTHER INFORMATION: Description of Artificial Sequence: Variant of
      SEQ ID No. 2
<220> FEATURE:
<221> NAME/KEY: VARIANT
<222> LOCATION: (5)
<223> OTHER INFORMATION: Xaa is Trp, Phe or Tyr.
<220> FEATURE:
<221> NAME/KEY: VARIANT
<222> LOCATION: (10)
<223> OTHER INFORMATION: Xaa is Trp, Phe or Tyr.
<220> FEATURE:
<221> NAME/KEY: VARIANT
<222> LOCATION: (13)
<223> OTHER INFORMATION: Xaa is Trp, Phe or Tyr.

<400> SEQUENCE: 13

Leu Glu Gln Ile Xaa Asn Asn Met Thr Xaa Met Gln Xaa Asp Lys
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Variant of
      SEQ ID No. 3
<220> FEATURE:
<221> NAME/KEY: VARIANT
<222> LOCATION: (5)
<223> OTHER INFORMATION: Xaa is Trp, Phe or Tyr.
<220> FEATURE:
<221> NAME/KEY: VARIANT
<222> LOCATION: (10)
<223> OTHER INFORMATION: Xaa is Trp, Phe or Tyr.
<220> FEATURE:
<221> NAME/KEY: VARIANT
<222> LOCATION: (13)
<223> OTHER INFORMATION: Xaa is Trp, Phe or Tyr.

<400> SEQUENCE: 14

Leu Thr Pro Asp Xaa Asn Asn Met Thr Xaa Gln Glu Xaa Glu Arg
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Variant of
      SEQ ID No 2
<220> FEATURE:
<221> NAME/KEY: VARIANT
<222> LOCATION: (7)
<223> OTHER INFORMATION: Xaa is Ala, Gly, Val, Leu, Ile, Phe, Trp, Tyr,
      Met, Cys, Ser, Thr, Gln, Glu, Asp, Lys, Arg, His or Pro

<400> SEQUENCE: 15

Leu Glu Gln Ile Trp Asn Xaa Met Thr Trp Met Gln Trp Asp Lys
 1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Variant of
      SEQ ID No. 2
<220> FEATURE:
<221> NAME/KEY: VARIANT
<222> LOCATION: (9)
<223> OTHER INFORMATION: Xaa is Ala, Gly, Val, Leu, Ile, Phe, Trp, Tyr,
      Met, Cys, Gln, Asp, Glu, Lys, Arg, His or Pro
```

<400> SEQUENCE: 16

Leu Glu Gln Ile Trp Asn Asn Met Xaa Trp Met Gln Trp Asp Lys
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Variant of
      SEQ ID No. 3
<220> FEATURE:
<221> NAME/KEY: VARIANT
<222> LOCATION: (7)
<223> OTHER INFORMATION: Xaa is Ala, Gly, Val, Leu, Ile, Phe, Trp, Tyr,
      Met, Cys, Ser, Thr, Gln, Asp, Glu, Lys, Arg, His or Pro

<400> SEQUENCE: 17

Leu Thr Pro Asp Trp Asn Xaa Met Thr Trp Gln Glu Trp Glu Arg
 1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Variant of
      SEQ ID No. 3
<220> FEATURE:
<221> NAME/KEY: VARIANT
<222> LOCATION: (9)
<223> OTHER INFORMATION: Xaa is Ala, Gly, Val, Leu, Ile, Phe, Trp, Tyr,
      Met, Cys, Gln, Asp, Glu, Lys, Arg, His or Pro

<400> SEQUENCE: 18

Leu Thr Pro Asp Trp Asn Asn Met Xaa Trp Gln Glu Trp Glu Arg
 1               5                  10                  15

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Nucleic
      acid of SEQ ID No. 2

<400> SEQUENCE: 19
ctggagcaga tctggaacaa catgacctgg atgcagtggg acaag            45

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Nucleid
      Acid of SEQ ID No. 2

<400> SEQUENCE: 20
ctggaacaga tttggaataa catgacctgg atggagtggg acaga            45

<210> SEQ ID NO 21
<211> LENGTH: 45
<212> TYPE: DNA

```
<213> ORGANISM: Artificial Sequence
<220> FEATURE:
<223> OTHER INFORMATION: Description of Artificial Sequence: Caveolin
      binding domain corresponding to amino acids 619 to 633 of HIV-1

<400> SEQUENCE: 21
ctggaacaga tttggaataa catgacctgg atgcagtggg acaaa          45
```